(12) United States Patent
Chen et al.

(10) Patent No.: US 8,962,855 B2
(45) Date of Patent: Feb. 24, 2015

(54) NITROGEN MUSTARD DERIVATIVES

(71) Applicant: Purdue Pharmaceutical Products L.P., Stamford, CT (US)

(72) Inventors: Yu Chen, San Jose, CA (US); Yi Chen, Lexington, MA (US)

(73) Assignee: Purdue Pharmaceutical Products, L.P., Stamford, CT (US)

( * ) Notice: Subject to any disclaimer, the term of this patent is extended or adjusted under 35 U.S.C. 154(b) by 0 days.

(21) Appl. No.: 14/347,397

(22) PCT Filed: Sep. 27, 2012

(86) PCT No.: PCT/US2012/057445
§ 371 (c)(1),
(2) Date: Mar. 26, 2014

(87) PCT Pub. No.: WO2013/049279
PCT Pub. Date: Apr. 4, 2013

(65) Prior Publication Data
US 2014/0303218 A1    Oct. 9, 2014

Related U.S. Application Data

(60) Provisional application No. 61/540,523, filed on Sep. 28, 2011.

(51) Int. Cl.
*C07D 417/12*    (2006.01)
*C07D 417/14*    (2006.01)
*A61K 31/427*    (2006.01)

(52) U.S. Cl.
CPC .............. *C07D 417/12* (2013.01); *C07D 417/14* (2013.01)
USPC .......................... 548/181; 548/185; 514/369

(58) Field of Classification Search
USPC ................................... 548/181, 185
See application file for complete search history.

(56) References Cited

U.S. PATENT DOCUMENTS 6,214,852 B1 *  4/2001  Kim et al. ................ 514/369

FOREIGN PATENT DOCUMENTS

| WO | WO-95/30442 A1 | 11/1995 |
| WO | WO-02/10161 A1 | 2/2002 |
| WO | WO-2009/036016 A1 | 3/2009 |
| WO | WO-2010/075542 A1 | 7/2010 |

OTHER PUBLICATIONS

Golub et al., Science, vol. 286, Oct. 15, 1999, pp. 531-537.*

* cited by examiner

*Primary Examiner* — Laura L. Stockton
(74) *Attorney, Agent, or Firm* — McCarter & English, LLP; Yu Lu

(57) ABSTRACT

The disclosure includes compounds of Formula (1): wherein $X_1$, $X_2$, Q, Z, $R_1$, and $R_2$ are defined herein. Also disclosed is a method for treating a neoplastic disease or an immune disease with these compounds.

Formula (1)

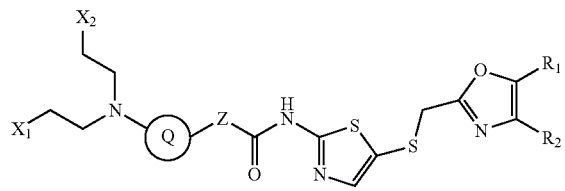

13 Claims, No Drawings

NITROGEN MUSTARD DERIVATIVES

RELATED APPLICATIONS

This application is a 371 of international application PCT/US2012/057445, filed Sep. 27, 2012 and entitled "Nitrogen Mustard Derivatives," which claims priority to and benefit of U.S. Provisional Application No. 61/540,523, filed on Sep. 28, 2011. The entire teachings of the above applications are incorporated herein by reference.

BACKGROUND

Cancer is one of the most life threatening diseases in which cells in a part of the body experience out-of-control growth. According to the latest data from American Cancer Society, cancer is the second leading cause of death in the United States (second only to heart disease) and claimed more than 550,000 lives in 2009. In fact, it is estimated that 50% of all men and 33% of all women living in the United States will develop some type of cancer in their lifetime. Therefore cancer constitutes a major public health burden and represents a significant cost in the United States. For decades, surgery, chemotherapy, and radiation were the established treatments for various cancers. Patients usually receive a combination of these treatments depending upon the type and extent of their disease. But the chemotherapy is most important option for cancer patient when the surgery treatment is impossible.

Nitrogen mustards, a kind of classic DNA alkylating agents, were among the first chemotherapeutic agents rationally applied to the treatment of cancer. Mechlorethamine, an analogue of mustard gas and derived from chemical warfare research during World War II, has been used in the cancer chemotherapy for over 60 years. Nitrogen mustards generally exert cytotoxic activity by forming DNA adducts or crosslinks between DNA strands under conditions present in cells, directly interfering with the reproductive cycle of the cell. The following are the structures of some well-known nitrogen mustards.

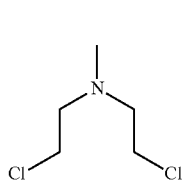
Mechlorethamine

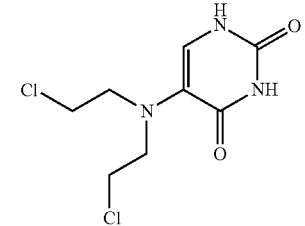
Uramustine

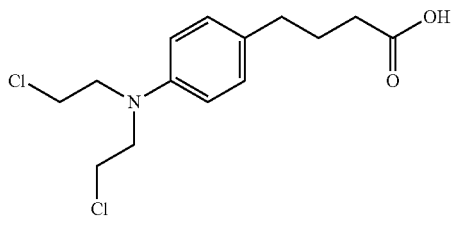
Chlorambucil

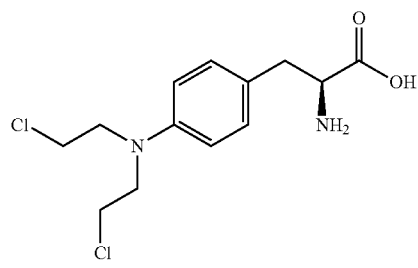
Melphalan

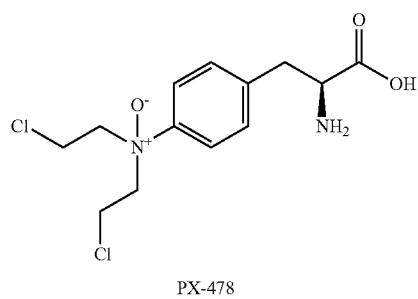
PX-478

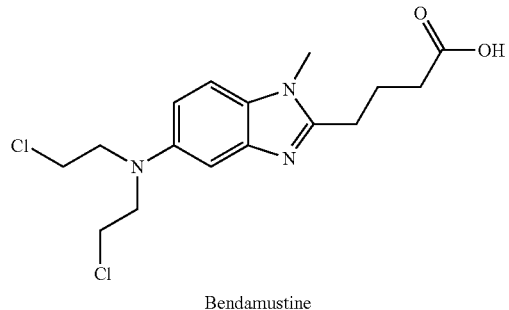
Bendamustine

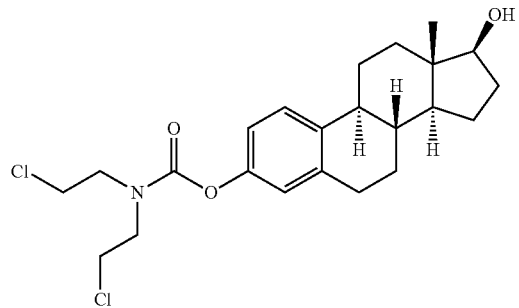
Estramustine

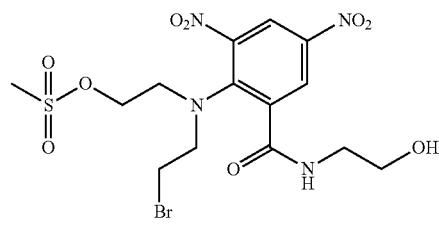
PR-104

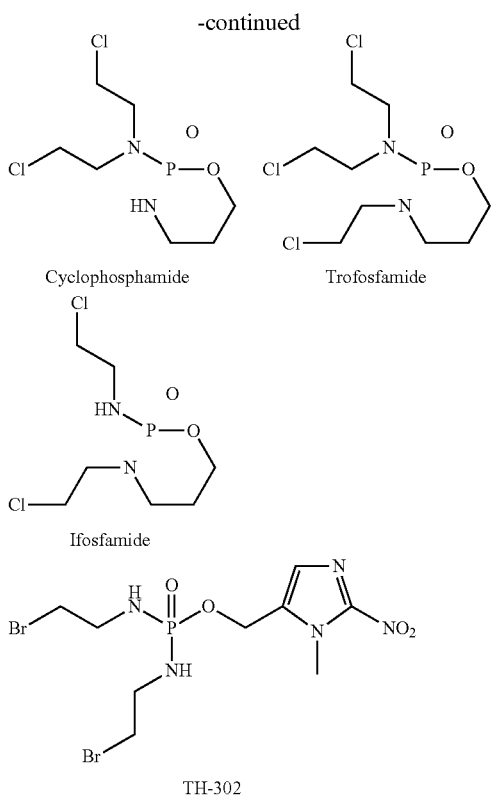

Melphalan is a well-known DNA alkylating nitrogen mustard approved for the treatment of multiple myeloma (Musto P, et al, *Expert Opin Investig Drugs,* 2007, 16(9):1467-87). Melphalan, in combination with Prednisone (MP), has been used as first line standard therapy for decades for elderly multiple myeloma patients ineligible for autologous stem cell transplantation. Currently, MP is still the backbone of new first-line MM chemotherapeutic regimens such as MP-thalidomide (MPT), MP-lenalidomide (MPR), and MP-bortezomib (MPV). In addition, the use of Melphalan alone as a conditioning regimen for autologous stem cell transplant is considered "Standard of Care" for multiple myeloma treatment. As for today, melphalan is in 196 active clinical trials for a variety of caner indications, such as multiple myeloma, leukemia, lymphoma, MDS, ovarian cancer, breast cancer, and brain tumor, etc.

Bendamustine, first synthesized in 1963, consists of an alkylating nitrogen mustard moiety and a purine-like benzimidazol moiety with a suggested purine-analog effect (Barman Balfour J A, et al, *Drugs* 2001; 61: 631-640). Bendamustine has been shown to have substantial activity against low-grade lymphomas (Herold M, et al., *Blood,* 1999; 94, Suppl 1: 262a), multiple myelomas (Poenisch W, et al., *Blood* 2000; 96, Suppl 1: 759a), and several solid tumors (Kollmannsberger C, et al., *Anticancer Drugs* 2000; 11: 535-539). It was also reported that bendamustine effectively induces apoptosis in lymphoma cells (Chow K U, et al., *Haematologica,* 2001; 86: 485-493). On March 2008, the FDA granted approval to market bendamustine for the treatment of chronic lymphocytic leukemia (CLL). On October 2008, the FDA granted further approval to market bendamustine for the treatment of indolent B-cell non-Hodgkin's lymphoma (NHL) that has progressed during or within six months of treatment with rituximab or a rituximab-containing regimen. Currently bendamustine is in clinical trials for a variety of caner indications, such as leukemia, lymphoma, small cell lung cancer, multiple myeloma, MDS, ovarian cancer, breast cancer, and brain tumor.

The nitrogen mustard Cyclophosphamide remains one of the most successful and widely utilized antineoplastic drugs in modem cancer therapy (Emadi A, et al, *Nat Rev Clin Oncol.* 2009 November; 6(11):638-47). Cyclophosphamide is an inactive prodrug that requires enzymatic and chemical activation and the resultant nitrogen mustard produces the interstrand and intrastrand DNA crosslinks that account for its cytotoxic properties. Cyclophosphamide based chemoregimens such as FCR, FCE, AC, and R-CHOP remains the cornerstone of first-line treatment for breast cancer, lymphoma, CLL, ovarian cancer, and soft tissue sarcomas.

Although the conventional DNA alkylating nitrogen mustards have made a significant contribution to cancer treatment, they have major limitations. As we know, the conventional DNA alkylating nitrogen mustards will damage the DNA and then the cellular DNA damage response pathway will be activated to arrest cell cycle progression, induce apoptosis, and repair the DNA damage. However, cancer cells treated with the conventional nitrogen mustards may easily escape from the cell cycle arrest and apoptosis, and may repair the DNA damage efficiently, leading to quick development of drug resistance and treatment failure. Therefore, it is urgent to continuously search in this field of art for the new generation nitrogen mustards with significantly improved anti-cancer activities.

Recently year, Cyclin-dependent kinases (CDK) has recently emerged as an important disease target for cancer treatment (Marcos Malumbres et al, *Nat Rev Cancer.* 2009 March; 9(3):153-66; Silvia Lapenna, et al, *Nat Rev Drug Discovery,* 2009 July; 8(7):547-66). CDKs are a family of serine/threonine kinases that regulate key cellular processes including cell cycle progression and RNA transcription (Shapiro G I. *J Clin Oncol.* 2006 Apr. 10; 24(11): 1770-83). Heterodimerized with regulatory cyclin units, CDKs can be generally divided into two groups based on their functions. The first group consists of core cell cycle components and governs the cell cycle transition and cell division: cyclin D-dependent kinases 4/6 and cyclin E-dependent kinase 2, which control the G→S transition; cyclin A-dependent kinases 1/2, a critical regulator of S-phase progression; cyclin B-dependent CDK1, required for the G2→M transition; and cyclin H/CDK7, the CDK-activating kinase. The second group, so called transcriptional CDKs, includes cyclin H/CDK7 and cyclin T/CDK9 which phosphorylate the C-terminal domain (CTD) of RNA polymerase II and promote transcriptional initiation and elongation.

The deregulation of the CDK activity is detected in virtually all forms of human cancer, most frequently due to the overexpression of cyclins and loss of expression of CDK inhibitors (de Career G et al, *Curr Med Chem.* 2007; 14(9): 969-85). CDK4/6 inhibition has been shown to induce potent G1 arrest in vitro and tumor regression in vivo (Lukas J et al., *Nature.* 1995 Jun. 8; 375(6531):503-6; Schreiber M et al., *Oncogene.* 1999 Mar. 4; 18(9):1663-76; Fry D W et al., *Mol Cancer Ther.* 2004 November; 3(11): 1427-38). Various approaches aimed at targeting CDK2/1 have been reported to induce S and G2 arrest followed by apoptosis (Chen Y N et al., *Proc Natl Acad Sci USA.* 1999 Apr. 13; 96(8):4325-9; Chen W et al., *Cancer Res.* 2004 Jun. 1; 64(11):3949-57; Mendoza N et al., *Cancer Res.* 2003 Mar. 1; 63(5):1020-4) Inhibition of the transcriptional CDKs 7 and 9 can affect the accumulation of transcripts encoding anti-apoptosis family members, cell cycle regulators, as well as p53 and NF-κB-responsive gene targets (Lam L T et al., *Genome Biol.* 2001; 2(10):RE- SEARCH0041). All these effects contribute to the induction of apoptosis and also potentiation of cytotoxicity mediated by disruption of a variety of pathways in many cancer cell types (Chen R et al., *Blood.* 2005 Oct. 1; 106(7):2513-9; Pepper C et al. *Leuk Lymphoma.* 2003 February; 44(2):337-42). CDKs are therefore recognized as an attractive target for the design and development of compounds that can specifically bind and inhibit the cyclin-dependent kinase activity and its signal transduction pathway in cancer cells, and thus can serve as therapeutic agents. As today, there is a list of CDk inhibitors, (e.g. AT-7519, AZD5438, Flavopiridol, P1446A-05, P276-00, CYC202, SCH 727965, BAY 1000394, LEE011, etc) currently in clinical trials for treatment of cancer.

SUMMARY

The present invention relates to a novel class of CDK-inhibiting derivatives of the conventional DNA alkylating nitrogen mustards. More specifically, the present invention relates to a novel class of rationally designed dual-functional DNA alkylating nitrogen mustard/CDk inhibitors in which a pharmacophore functionally capable of inhibiting CDK is covalently linked to the nitrogen mustard pharmacophore. By attacking the cancer cells from two distinct directions simultaneously (CDK inhibition and DNA-alkylation), the single dual-functional molecule may improve drug efficacy of the conventional DNA alkylating nitrogen mustards and prevent the emergence of drug resistance without increasing the dose-limiting toxicities. Thus, the compounds of the present invention may be useful in treating a patient having a tumor. The compounds of the invention may also useful in the prevention and treatment of an immune disease.

In one aspect, this invention relates to the compounds of Formula (1):

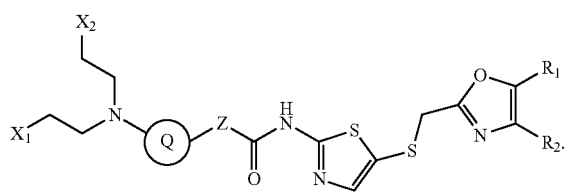

Formula (1)

In Formula (1), each of $X_1$ and $X_2$ independently, is halo or $OSO_2R_a$, in which $R_a$ is alkyl, alkenyl, or alkynyl; Q is cycloalkyl, heterocycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —CH=NH, cyano, alkyl-$R_b$, CH=NOR$_b$, OR$_b$, OC(O)R$_b$, OC(O)OR$_b$, OC(O)SR$_b$, SR$_b$, C(O)R$_b$, C(O)OR$_b$, C(O)SR$_b$, C(O)NR$_c$R$_d$, SOR$_b$, SO$_2$R$_b$, NR$_c$R$_d$, alkyl-NR$_c$R$_d$, or N(R$_c$)C(O)R$_d$, in which each of R$_b$, R$_c$, and R$_d$, independently, is H, alkyl, alkenyl, alkynyl, cycloalkyl, heterocycloalkyl, aryl, heteroaryl, halo, cyano, nitro, amino, hydroxyl, alkylamino, haloalkyl, or alkoxy; Z is deleted or (CH$_2$)$_m$ in which m is an integer from 1 to 10; and each of R$_1$ and R$_2$ independently, is H, alkyl, alkenyl, alkynyl, cycloalkyl, heterocycloalkyl, cycloalkenyl, heterocycloalkenyl, aryl, heteroaryl, halo, nitro, oxo, —CH=NH, cyano, alkyl-R$_b$, CH=NOR$_b$, OR$_b$, OC(O)R$_b$, OC(O)OR$_b$, OC(O)SR$_b$, SR$_b$, C(O)R$_b$, C(O)OR$_b$, C(O)SR$_b$, C(O)NR$_c$R$_d$, SOR$_b$, SO$_2$R$_b$, NR$_c$R$_d$, alkyl-NR$_c$R$_d$, or N(R$_c$)C(O)R$_d$.

One subset of the compounds with Formula (1) includes those in which $R_1$ is H, alkyl, alkenyl, or alkynyl and $R_2$ is H. A further subset of these compounds represented by Formula (2):

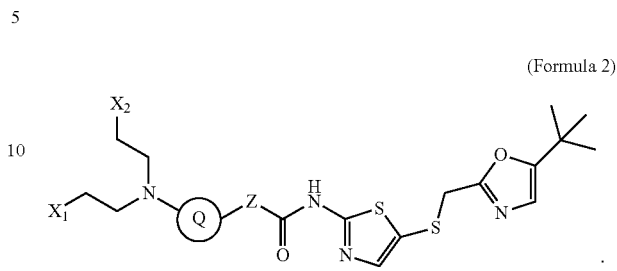

(Formula 2)

One subset of the Formula (2) compounds includes those in which Q is an aryl or heteroaryl. In these compounds, Q can be a 5-6 membered aryl or heteroaryl (e.g.

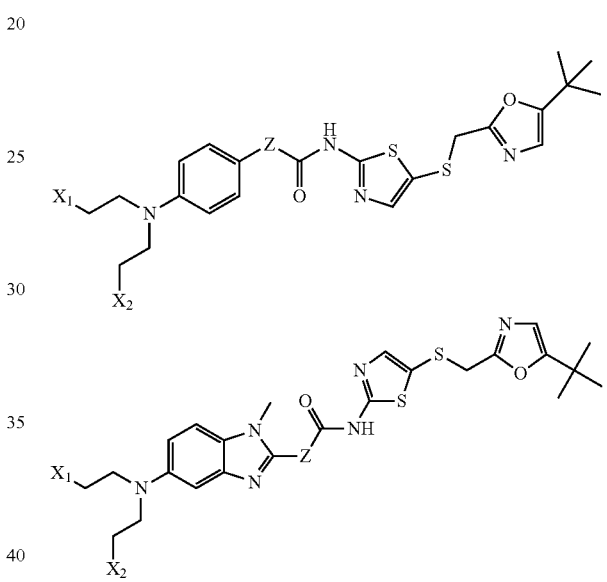

Compounds of the invention may contain one or more asymmetric carbon atoms. Accordingly, the compounds may exist as diastereomers, enantiomers or mixtures thereof. Each of the asymmetric carbon atoms may be in the R or S configuration and both of these configurations are within the scope of the invention.

The compounds described above include the compounds themselves, as well as their salts, their solvates, and their prodrugs, if applicable. A salt, for example, can be formed between an anion and a positively charged group (e.g., amino) on a compound of this invention. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a compound of this invention. Suitable cations include sodium ion, potassium ion, magnesium ion, calcium ion, and an ammonium cation such as tetramethylammonium ion. The compounds of this invention also include those salts containing quaternary nitrogen atoms. Examples of prodrugs include esters and other pharmaceutically acceptable derivatives, which, upon administration to a subject, are capable of providing active compounds described herein.

Also within the scope of this invention is a pharmaceutical composition containing one or more of the above-described compounds for use in treating a neoplastic or immune disorder, as well as this therapeutic use and use of the compounds for the manufacture of a medicament for treating the disorder.

A modified compound of any one of the above-described compounds including a modification having an improved (e.g., enhanced, greater) pharmaceutical solubility, stability, and/or bioavailability as compared to the unmodified compound is also contemplated.

This invention also relates to a method of treating a neoplastic disorder (e.g., cancer, myelodysplastic syndrome, or myeloproliferative disease) by administering to a subject in need thereof an effective amount of one or more of the compounds, compositions, and/or salts and modifications thereof described above.

Furthermore, this invention relates to a method of treating an immune disease (e.g., rheumatoid arthritis and multiple sclerosis) by administering to a subject in need thereof an effective amount of one or more of the compounds, compositions, and/or salts and modifications thereof described above.

The details of one or more embodiments of the invention are set forth in the description below. Other features, objects, and advantages of the invention will be apparent from the description and from the claims.

DETAILED DESCRIPTION

Exemplary compounds described herein include, but are not limited, to the following:

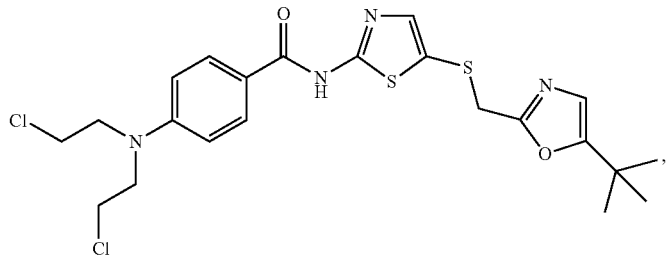

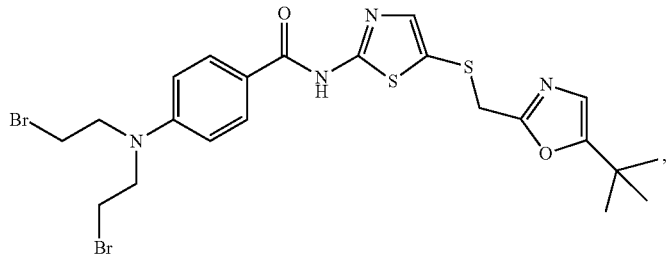

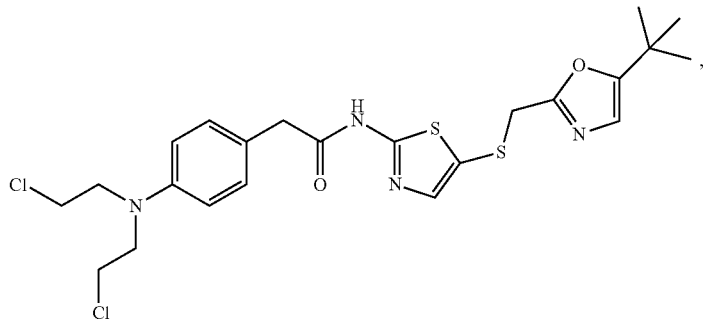

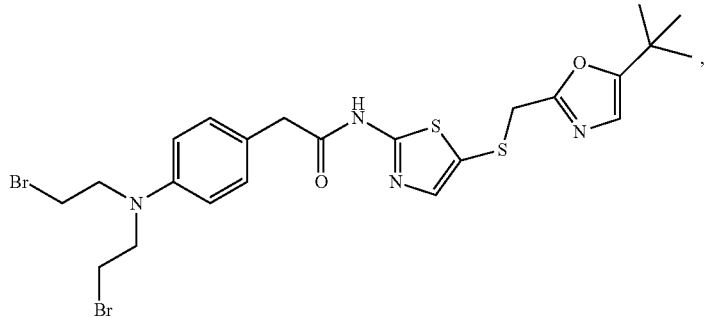

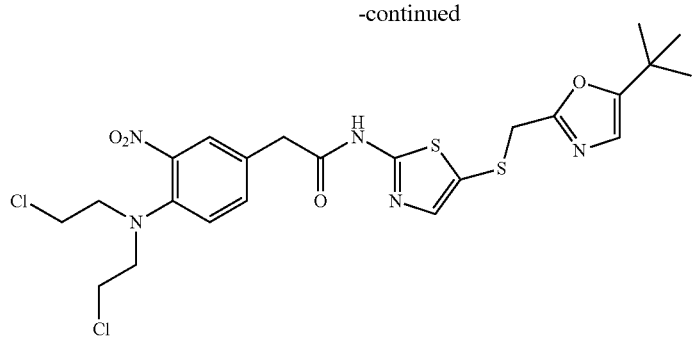
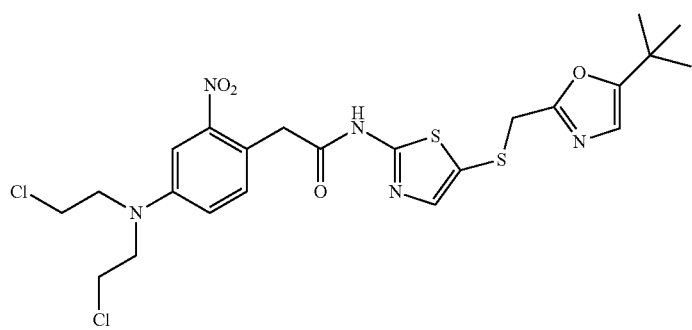
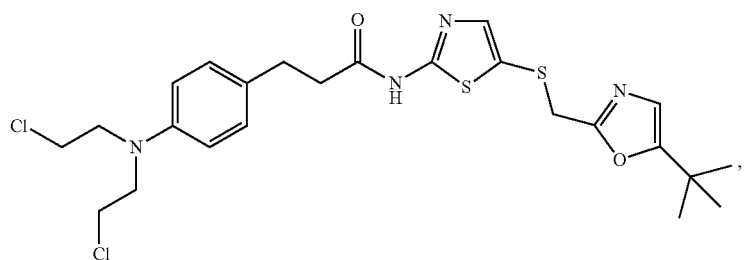
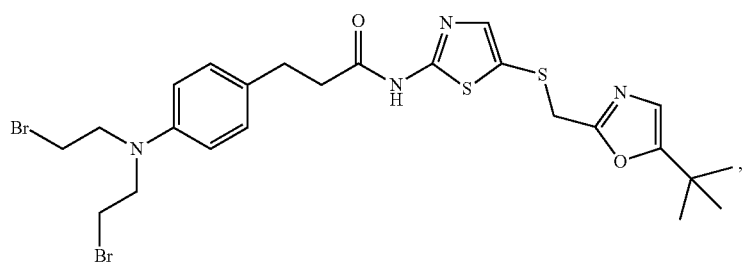
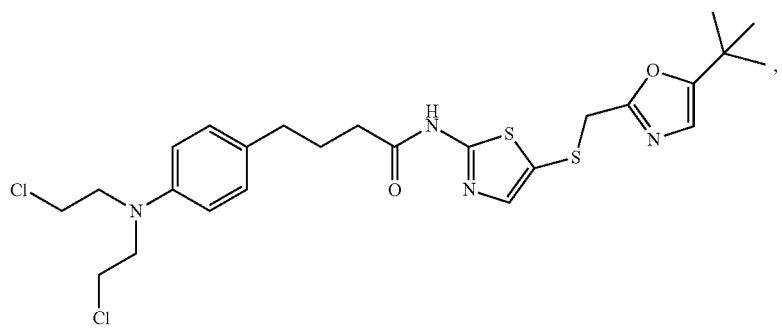

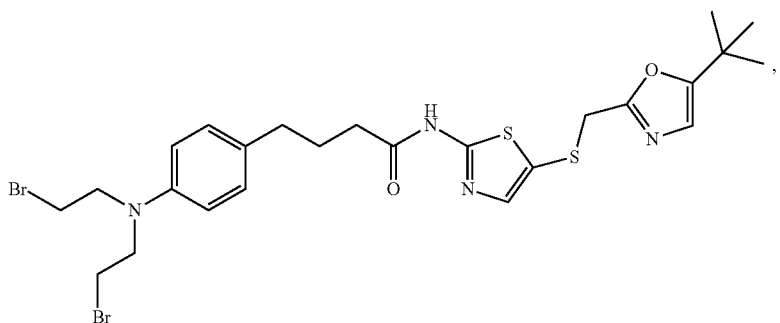
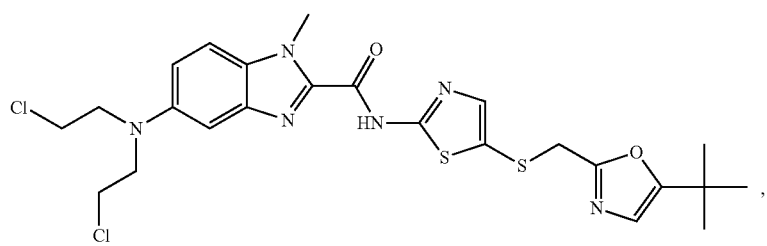
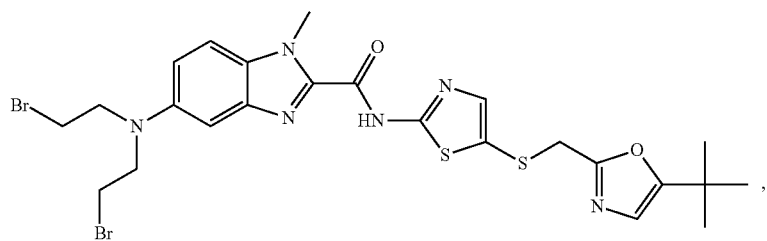
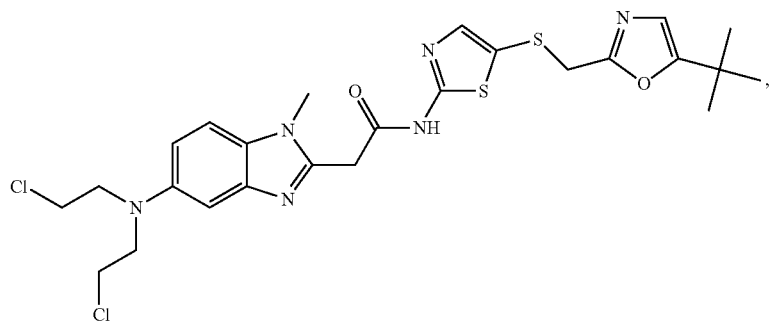
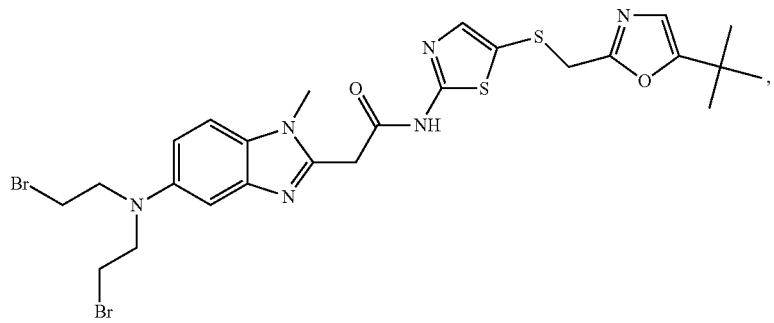

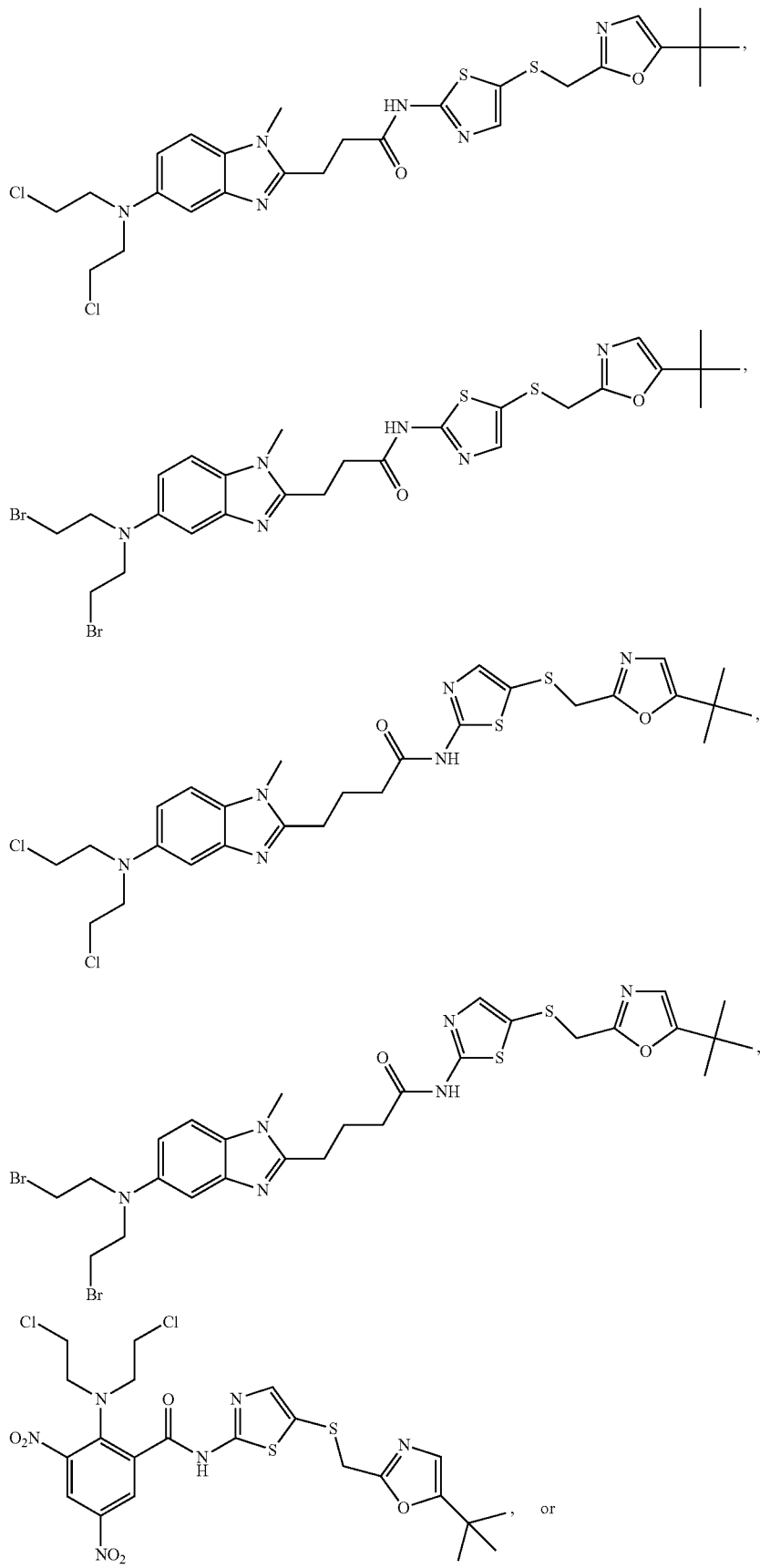

-continued

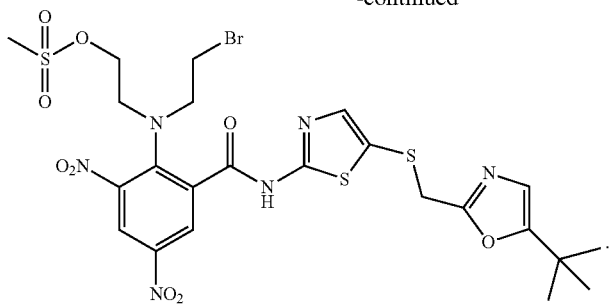

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

It should be recognized that the compounds of the present invention may be present and optionally administered in the form of salts, solvates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art. Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), *Bioorganic and Medicinal Chemistry Letters*, Vol. 4, p. 1985.

The invention further encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compound according to the present invention exhibit insufficient solubility, methods for solubilizing the compounds may be used. Such methods are known to those of skill in this art, and include, but are not limited to, pH adjustment and salt formation, using cosolvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of compositions may be used in conjunction with the compounds of the present invention. Such compositions may include, in addition to the compounds of the present invention, pharmaceutical excipients, and other conventional, pharmaceutically inactive agents. Additionally, the compositions may include active agents in addition to the compounds of the present invention. These additional active agents may include additional compounds according to the invention, or one or more other pharmaceutically active agents.

Furthermore, the compositions of the present invention may be in the form of controlled release or immediate release formulations.

A wide variety of administration methods may be used in conjunction with the compounds of the present invention. Compositions comprising the compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms. Compositions may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

"Combination therapy" includes the administration of the subject compounds in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, preferably compounds that are able to enhance the effect of the compounds of the invention. The compounds of the invention can be administered simultaneously (as a single preparation or separate preparation) or sequentially to the other drug therapy. In general, a combination therapy envisions administration of two or more drugs during a single cycle or course of therapy.

In certain preferred embodiments, the compounds of the invention are administered in combination with a chemotherapeutic agent. Chemotherapeutic agents encompass a wide range of therapeutic treatments in the field of oncology.

These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as mustard gas derivatives (Mechlorethamine, cyclophospamide, chlorambucil, melphalan, trofosfamide), ethylenimines (thiotepa, hexamethylmelanine), Alkylsulfonates (Busulfan), Hydrazines and Triazines (Altretamine, Procarbazine, Dacarbazine and Temozolomide), Nitrosureas (Carmustine, Lomustine and Streptozocin), Ifosfamide and metal salts (Carboplatin, Cisplatin, and Oxaliplatin); plant alkaloids such as Podophyllotoxins (Etoposide and Tenisopide), Taxanes (Paclitaxel and Docetaxel), Vinca alkaloids (Vincristine, Vinblastine and Vinorelbine); anti-tumor antibiotics such as Chromomycins (Dactinomycin and Plicamycin), Anthracyclines (Doxorubicin, Daunorubicin, Epirubicin, Mitoxantrone, and Idarubicin), and miscellaneous antibiotics such as Mitomycin and Bleomycin; anti-metabolites such as folic acid antagonists (Methotrexate), pyrimidine antagonists (5-Fluorouracil, Foxuridine, Cytarabine, Capecitabine, and Gemcitabine), purine antagonists (6-Mercaptopurine and 6-Thioguanine) and adenosine deaminase inhibitors (Cladribine, Fludarabine, Nelarabine and Pentostatin); topoisomerase inhibitors such as topoisomerase I inhibitors (Ironotecan, topotecan) and topoisomerase II inhibitors (Amsacrine, etoposide, etoposide phosphate, teniposide); monoclonal antibodies (Alemtuzumab, Gemtuzumab ozogamicin, Rituximab, Trastuzumab, Ibritumomab Tioxetan); and miscellaneous anti-neoplastics such as ribonucleotide reductase inhibitors (Hydroxyurea); adrenocortical steroid inhibitor (Mitotane); enzymes (Asparaginase and Pegaspargase); anti-microtubule agents (Estramustine); and retinoids (Bexarotene, Isotretinoin, Tretinoin (ATRA).

In certain preferred embodiments, the compounds of the invention are administered in combination with a targeted anti-cancer agent. Targeted anti-cancer agents encompass a wide range of therapeutic treatments in the field of oncology. Examples of such agents include, but are not limited to, the compounds functionally capable of inhibiting the activity of tyrosine kinase, seronine/threonine kinases, DNA methyl transferases (DNMT), proteasomes, and heat-shock proteins (HSPs), vascular endothelial growth factor receptor (VEGFR), platelet-derived growth factor receptor (PDGFR), fibroblast growth factor receptor (FGFR), mitogen-activated protein kinase (MAPK/MEK), cyclin-dependent kinase (CDK), Histone deacetylases (HDAC), and the phosphatidylinositol 4,5-bisphosphate-AKT-mammalian target of the rapamycin pathway [P13K-AKT (RAF, mTOR)], matrix metalloproteinase, farnesyl transferase, and apoptosis.

In certain preferred embodiments, the compounds of the invention are administered in combination with a chemoprotective agent, immunotherapeutic agents, vaccines, or antibodies. Chemoprotective agents act to protect the body or minimize the side effects of chemotherapy. Examples of such agents include, but are not limited to, amfostine, mesna, and dexrazoxane.

In certain preferred embodiments, the subject compounds are administered in combination with radiation therapy. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The invention further relates to a pharmaceutical composition for the treatment of a neoplastic disorder in a mammal which comprises a therapeutically-effective amount of the compound represented by Formula I, or a pharmaceutically acceptable salt, a hydrate, a solvate, a prodrug, an antive metabolite, a corresponding enantiomer, a corresponding racemate, or a corresponding diastereomer thereof.

In a preferred embodiment, wherein said neoplastic disease is selected from the group consisting of lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome and myeloproliferative disease.

It is well known that immunosuppression is one of major side-effect of the conventional chemotherapeutical agents such as nitrogen mustard. At low dose, the chemotherapeutical agent can be used to treat immune diseases such as multiple sclerosis, rheumatoid arthritis and the suppression of transplant rejections. For example, nitrogen mustard Cyclophosphamide is a very potent immunosuppressive agent (Emadi A, et al, *Nat Rev Clin Oncol.* 2009 November; 6(11): 638-47; Perini P, et al. *Neurol Sci.* 2008 September; 29 Suppl 2:S233-4.) and is also widely used in bone marrow transplantation "conditioning" and "mobilization" regimens, and for the treatment of refractory severe autoimmune conditions, such as systemic lupus erythematosus (SLE), minimal change disease, severe rheumatoid arthritis, Wegener's granulomatosis (with trade name Cytoxan), scleroderma, and multiple sclerosis (with trade name Revimmune). In addition, CDK inhibitors are emerging as a new class of immunosuppressive agent. For example, it was found that the CDK activity may be a useful target in the treatment of systemic lupus erythematosus. (Zoj a C, et al. *Arthritis Rheum.* 2007 May; 56(5):1629-37). A direct immunomodulatory action of CDK inhibitor seliciclib on T cells and B cells may be one of the mechanisms underlying the beneficial effects. In another paper (Sekine C et al, *J Immunol.* 2008 Feb. 1; 180(3):1954-61), the successful treatment of animal models of rheumatoid arthritis with small-molecule cyclin-dependent kinase inhibitors has been reported. Therefore it is not difficult to imagine that a dual functional nitrogen mustard/CDK inhibitor represented by Formula (I) could be used for treatment of an immune disease. The invention further relates to a pharmaceutical composition for the treatment of an immune disease in a mammal which comprises a therapeutically-effective amount of the compound of Formula I, or a pharmaceutically acceptable salt, a hydrate, a solvate, a prodrug, an antive metabolite, a corresponding enantiomer, a corresponding racemate, or a corresponding diastereomer thereof.

In a preferred embodiment, the immune disease is selected from the group consisting of the rejection of transplanted organs and tissues, a graft-versus-host disease, a non-autoimmune inflammatory disease, and an autoimmue disease, wherein said autoimmue disease is selected from the group consisting of acute disseminated encephalomyelitis, addison's disease, ankylosing spondylitis, antiphospholipid antibody syndrome, autoimmune hemolytic anemia, autoimmune hepatitis, autoimmune inner ear disease, bullous pemphigoid, coeliac disease, chagas disease, chronic obstructive pulmonary disease, churg-strauss syndrome, dermatomyositis, Crohn's disease, diabetes mellitus type 1, endometriosis, goodpasture's syndrome, graves' disease, guillain-barré syndrome, hashimoto's disease, hidradenitis suppurativa, idiopathic thrombocytopenic purpura, interstitial cystitis, lupus erythematosus, morphea, multiple sclerosis, myasthenia gravis, narcolepsy, neuromyotonia, pemphigus vulgaris, pernicious anaemia, polymyositis, primary biliary cirrhosis, psoriasis, psoriatic arthritis, rheumatoid arthritis, schizophrenia, scleroderma, temporal arteritis, vasculitis, vitiligo, and wegener's granulomatosis.

It should be understood that the invention is not limited to the particular embodiments shown and described herein, but that various changes and modifications may be made without departing from the spirit and scope of the invention as defined by the claims.

DEFINITIONS

"Acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl. "Alkoxy" means an oxygen moiety having a further alkyl substituent. "Alkoxycarbonyl" means an alkoxy group attached to a carbonyl group. "Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl. The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl. The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NRaRb where Ra and Rb are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality. A mixture of the two enantiomeric forms is termed a "racemic mixture".

"Nitro" means the radical —NO$_2$.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, Protecting Groups in Organic Synthesis, 3rd edition, John Wiley & Sons, 1999.

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, for example phenylsulfide; aralkylsulfide, for example benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases.

"Prodrug" means a compound that is convertible in vivo metabolically into an inhibitor according to the present invention. For example, an inhibitor comprising a hydroxyl group may be administered as an ester that is converted by hydrolysis in vivo to the hydroxyl compound.

"Pharmacophore", as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well known drug topotecan and irinotecan. As another example, nitrogen mustard pharmacophore has a typical formula of —N(CH$_2$CH$_2$X)$_2$ or its N-oxide analogues in which X is a leaving group such as halo. The anti-cancer drugs containing a nitrogen mustard pharmacophore include but not limited to Melphalan, Bendamustine, Cyclophosphamide, PX-478, TH-302, PR-104, Ifofamide, and so on.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. A "subject" refers to a human and a non-human animal. Examples of a non-human animal include all vertebrates, e g, mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

Synthetic Methods

The compounds of the inventions may be prepared by any process known in the field. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

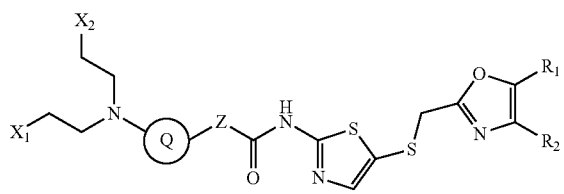

In general, compounds with Formula (1) can be prepared by the following Scheme 1 wherein $X_1$, $X_2$, Q, Z, $R_1$, and $R_2$, are the same as those described in the Summary section above.

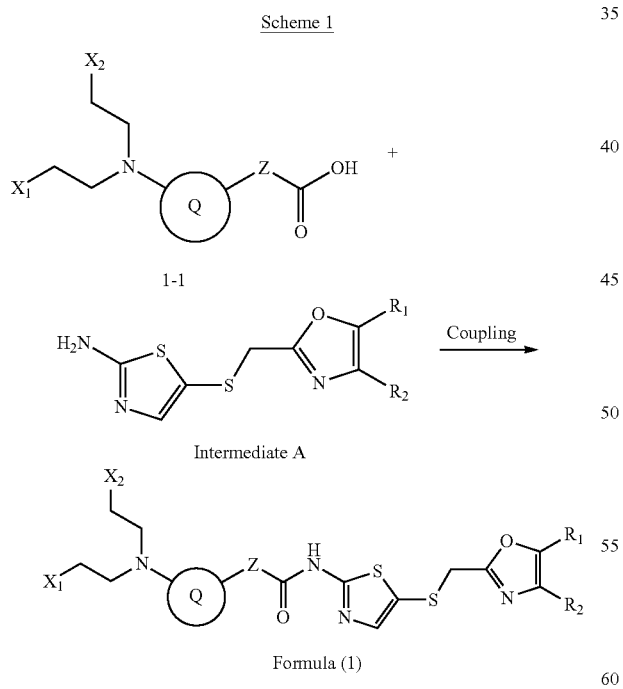

Scheme 1

Formula (1)

As shown in Scheme 1, the Intermediate A can be coupled with an appropriate nitrogen mustard with a carboxylic acid tail (1-1) to afford the target molecules with formula (I). A number of coupling agent, like DCC(N,N'-dicyclohexylcarbodiimide), DIC(N,N'-diisopropylcarbodiimide), EDC (also EDAC or EDCI, acronyms for 1-ethyl-3-(3-dimethylaminopropyl) carbodiimide, HBTU (O-(Benzotriazol-1-yl)-N,N,N',N'-tetramethyluronium hexafluorophosphate), TBTU (O-(Benzotriazol-1-yl)-N,N,N',N'-tetramethyluronium tetrafluoroborate), HATU (O-(7-Azabenzotriazol-1-yl)-N,N,N',N'-tetramethyluronium hexafluorophosphate), HCTU (O-(6-Chlorobenzotriazol-1-yl)-N,N,N',N'-8 tetramethyluronium hexafluorophosphate), could be used for the coupling reaction.

The Intermediate A in Scheme 1 can be prepared by the following Scheme 2-A and 2-B, in which $R_1$, and $R_2$, are the same as those described in the Summary section above.

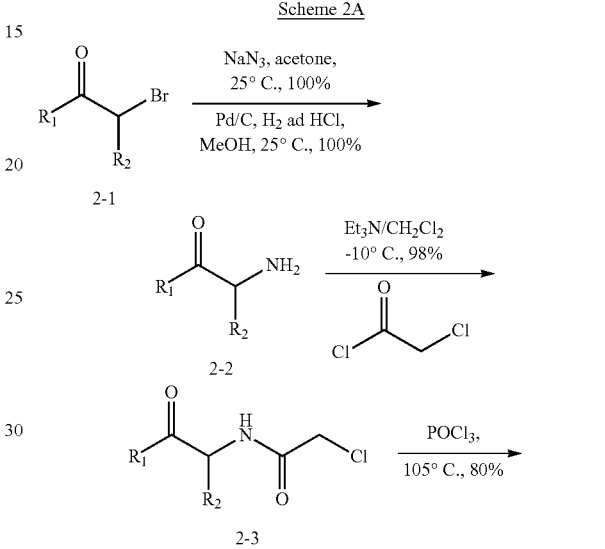

Scheme 2A

Scheme 2B

Intermediate A

As shown in Scheme 2-A, the starting material 2-1 can be converted smoothly to 2-2 by treatment with sodium azide followed by catalytic hydrogenation. Acylation of 2-2 with chloroacetyl chloride will afford ketoamide 2-3 which will be cyclized to the intermediate chloromethyloxazole 2-4 in refluxing phosphorus oxychloride. In Scheme 2-B, the thiazole core can be elaborated by treatment of commercially available 2-aminothiazole (2-5) with bromine and potassium thiocyanate to give 2-6 in a low yield but moderately scalable process. Reduction of 2-6 by exposure to sodium borohydride in methanol followed by alkylation of the resulting thiolate with chloromethyloxazole 2-4 will lead to Intermediate A.

The preparation of nitrogen mustard 1-1 shown in scheme 1 is well-known in the field. For example, the 1-1 nitrogen mustard in which $X_1$ is the same as $X_2$ (e.g Cl) can be prepared by the following Scheme 3.

Scheme 3

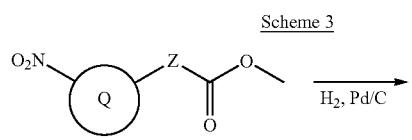

3-1

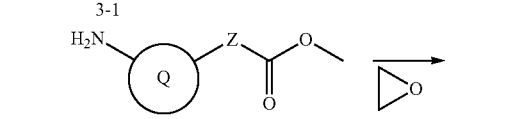

3-2

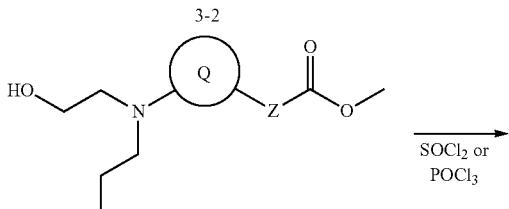

3-3

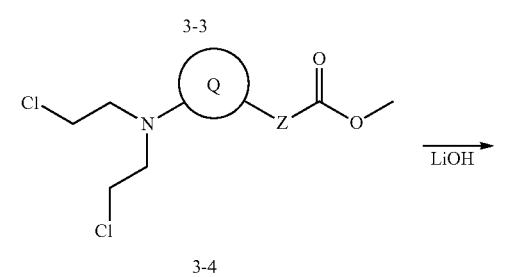

3-4

1-1

The starting material (3-1) can be reduced, for example with $H_2$, Pd/C, to an amino-substituted intermediate (3-2). The resulting intermediate (3-2) can be easily converted to intermediate (3-3) and then intermediate (3-4) by standard organic synthesis techniques with high yield. The hydrolysis of intermediate (3-4) in LiOH can afford the nitrogen mustard 1-1.

For the asymmetric nitrogen mustard 1-1 in which $X_1$ is different from $X_2$ (e.g $X_1$ is Br and $X_1$ is —OSO$_2$CH$_3$) can be prepared by the following scheme 4.

Scheme 4

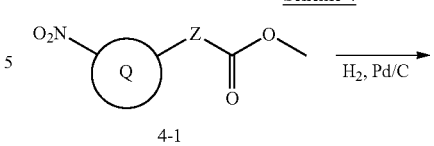

4-1

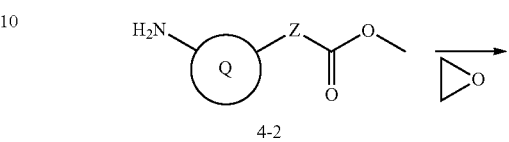

4-2

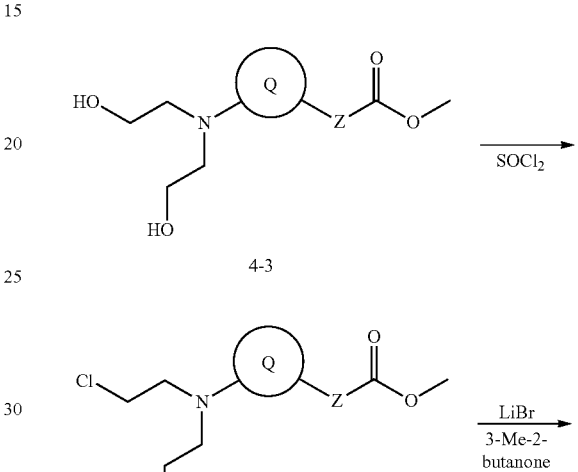

4-3

4-4

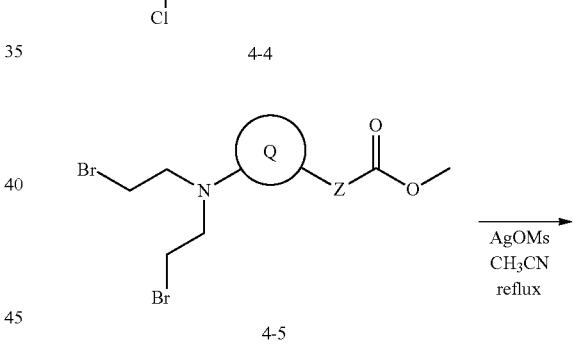

4-5

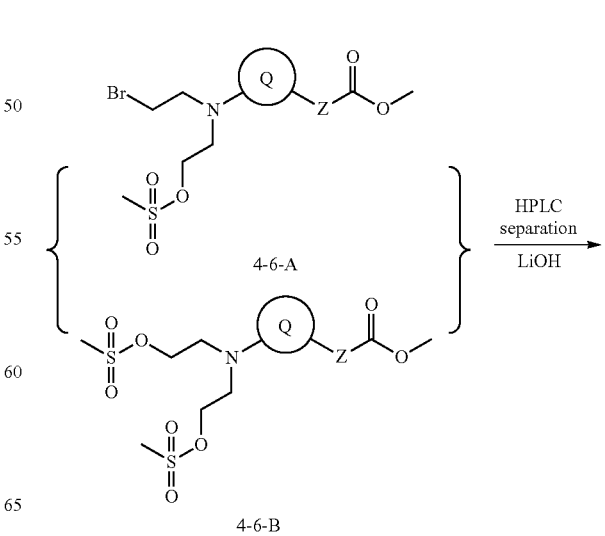

4-6-A 4-6-B

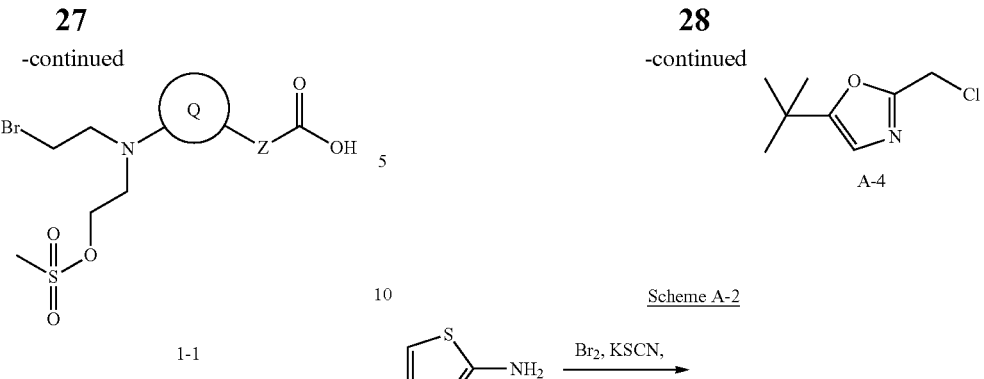

The starting material (4-1) can be reduced, for example with H$_2$, Pd/C, to an amino-substituted intermediate (4-2). The resulting intermediate (4-2) can be easily converted to intermediate (4-3) and then intermediate (4-4) by standard organic synthesis techniques with high yield. Replacement of the chloride groups of (4-4) with LiBr in boiling 3-methyl-2-butanone gives dibromide (4-5), which is further substituted with silver methanesulfonate in refluxing acetonitrile to produce a mixture of mono- and dimesylates (4-6-A) and (4-6-B), separable by column chromatography. The hydrolysis of intermediate (4-6-A) in LiOH can afford the asymmetric nitrogen mustard 1-1.

EXAMPLES

Example 1

Preparation of Intermediate CY-200

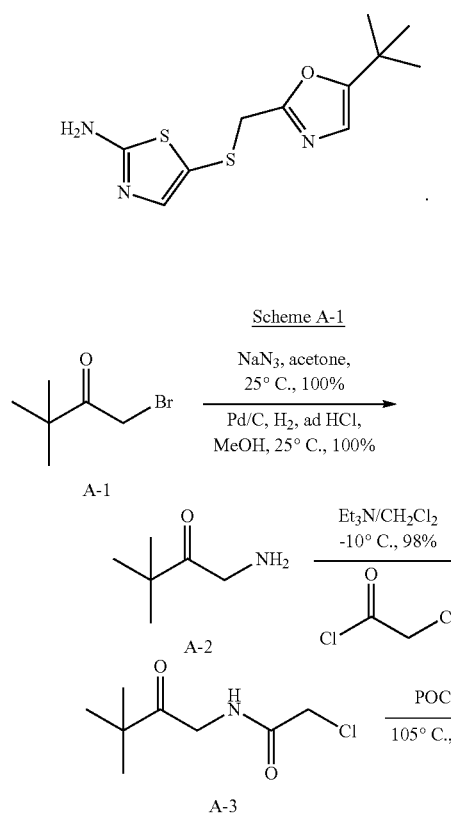

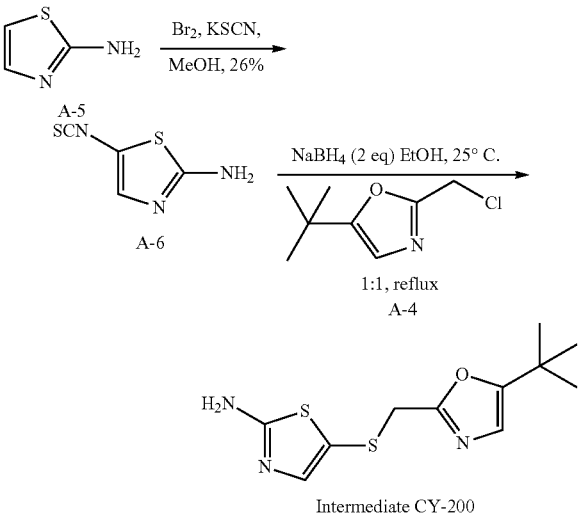

Step 1: To a 2 L three-necked round-bottom flask fitted with a mechanical stirrer was added bromopinacolone A-1 (134 g, 747 mmol, 1.0 equiv), acetone (1.2 L), and sodium azide (63.2 g, 971 mmol, 1.3 equiv). The reaction mixture was stirred at room-temperature overnight and then filtered, and the solids were washed with acetone (2×100 mL). The filtrate was concentrated in vacuo to provide azidopinacolone (105.0 g, 100%) as an oil. The crude material was used in the next step without further purification.

Step 2: To a 2 L three-necked round-bottom flask fitted with a mechanical stirrer were added azidopinacolone (28.6 g, 203 mmol, 1.0 equiv), methanol (1145 mL), concentrated HCl (18 mL), and 10% Pd/C (3.5 g, 50% water wet). The reaction mixture was stirred under hydrogen at 20 psi for 2 h, the mixture was filtered through a pad of Celite, and the residue rinsed with methanol (2×50 mL). The filtrate was concentrated under reduced pressure at a temperature below 40° C. The resulting wet solid was azeotroped with 2-propanol (2×100 mL), anhydrous ether (100 mL) was added, and the slurry which formed was stirred for 5 min. The solid product was collected by filtration, and the cake was washed with diethyl ether (2×30 mL) and then dried in vacuo to give aminopinacolone hydrochloride A-2.

Step 3: To a 1 L three-necked round-bottom flask fitted with a mechanical stirrer were added aminopinacolone hydrochloride A-2 (15.2 g, 100 mmol, 1.0 equiv) and CH$_2$Cl$_2$ (350 mL). The slurry was cooled to −5° C., and triethylamine (35 mL, 250 mmol, 2.5 equiv) was added. The resulting mixture was stirred and cooled to −10° C. A solution of chloroacetyl chloride (8.8 mL, 110 mmol, 1.1 equiv) in CH$_2$Cl$_2$ (20 mL) was added dropwise over 15 min while keeping the reaction temperature below −5° C. The reaction was stirred for 1 h and then quenched with 1 N aq HCl (200 mL). The phases were separated, and the organic phase was washed with 1 N aq HCl (200 mL), and water (50 mL), dried (Na2SO4), and concentrated in vacuo to afford A-3 (18.9 g, 98%) as a white solid.

Step 4: To a 100 mL rounded bottom flask fitted with a magnetic stirrer were added A-3 (18.9 g, 98.6 mmol, 1 equiv) and POCl3 (38 mL, 407 mmol, 4.1 equiv). The reaction mixture was heated to 105° C. and stirred for 1 h. After being cooled to room temperature, the reaction mixture was poured carefully into ice (180 g). The mixture was extracted with ether (6×150 mL). The organic extracts were combined and neutralized to pH 7-8 with saturated sodium bicarbonate (~700 mL). The organic phase was separated and washed successively with saturated sodium bicarbonate (100 mL), water (100 mL), and brine (50 mL), dried (MgSO4), and concentrated in vacuo. The crude material was distilled under reduced pressure to give A-4 as a colorless oil.

Step 5: A-6 was prepared from A-5 according to the paper of *J. Heterocycl. Chem.* 1984, 21, 401-406. To a solution of thiocyanate A-6 (10.0 g, 63.3 mmol) in absolute EtOH (600 mL) was added NaBH4 (4.8 g, 120 mmol) portionwise at room temperature. The mixture was stirred for 1 h, and then acetone (300 mL) was slowly introduced. After 1 h, a solution of oxazole chloride A-4 (12.0 g, 69 mmol) in EtOH (100 mL) was added, and the resulting dark reaction mixture heated to reflux for 1 h. The resulting mixture was cooled, concentrated in vacuo, and then partitioned between EtOAc and brine. The organic phase was separated, dried (MgSO4), and concentrated in vacuo to give a crude solid. The crude material was triturated with diethyl ether/hexane to provide Intermediate CY-200 (16.0 g, 94%) as a pale red-brown solid. LC/MS: 270.1 [M+H]+.

Example 2

Preparation of CY-201

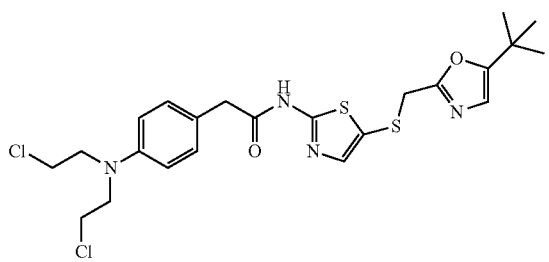 [SMILES: CC(C)(C)c1cnc(CSc2cnc(NC(=O)Cc3ccc(N(CCCl)CCCl)cc3)s2)o1]

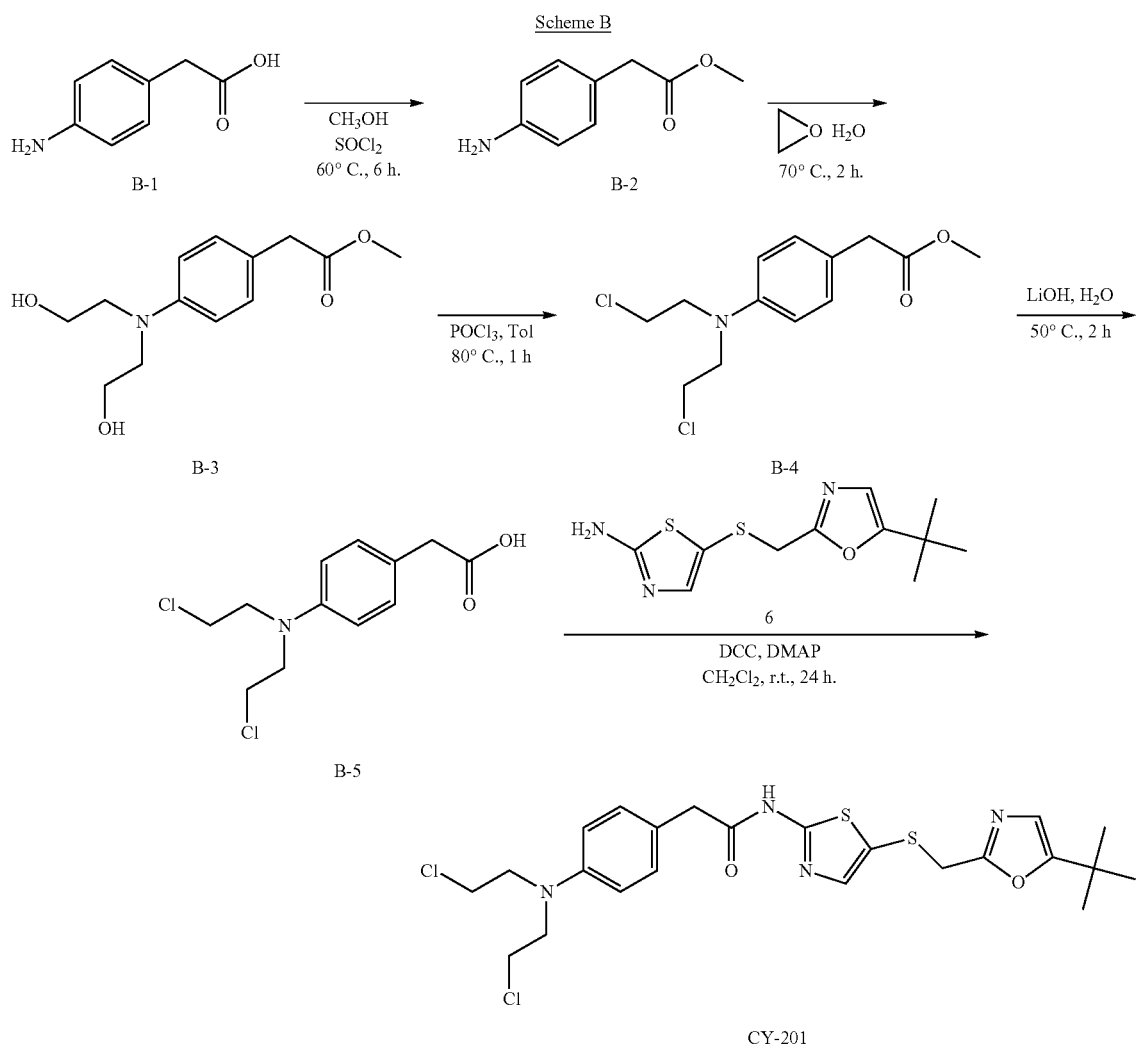

Step 1: Synthesis of methyl 2-(4-aminophenyl)acetate (B-2): To a solution of 2-(4-aminophenyl)acetic acid (B-1) (10 g, 66.16 mmol) in methanol (50 mL) was added dropwise SOCl$_2$ (5 mL). The mixture was stirred at 60° C. for 6 h. After evaporated the solvent, the residue was recrystallized with Et$_2$O to afford the product (10.9 g, 99%) as a yellow solid. LC-MS: (M+H)$^+$=166;

Step 2: Synthesis of methyl 2-(4-(bis(2-hydroxyethyl) amino)phenyl)acetate (B-3): To a solution of Methyl 2-(4-aminophenyl)acetate (B-2) (10.9 g, 65.98 mmol) in water (100 mL) was added oxirane (25 mL) at 0° C. Then the cloudy mixture was heated to 70° C. with vigorous stirring for 2 hrs, the solution was evaporated and extracted with EtOAc (150 ml*3), the organic phase was dried over Na$_2$SO$_4$. Filtration and concentration in vacuo gave the crude residue. The residue was recrystallized with hexane to afford the product (8.5 g, 51%) as a gray solid. LC-MS: (M+H)$^+$=254;

Step 3: Synthesis of methyl 2-(4-(bis(2-chloroethyl) amino)phenyl)acetate (B-4): To a solution of methyl 2-(4-(bis (2-hydroxyethyl)amino)phenyl)acetate (B-3) (6.0 g, 23.69 mmol) in toluene (30 ml) was added Phosphoryl chloride (6 ml) at 0° C. The mixture was stirred at 80° C. for 1 h, then the mixture was cooled down to r.t. and stirred with aqueous sodium hydrogen carbonate, and extracted with CH$_2$Cl$_2$ (30 ml*3). The organic layer was separated, washed with water and brine, and dried over Na$_2$SO$_4$. Filtration and concentration in vacuum gave the crude residue. The residue was purified by silica gel chromatography eluting with PE to EtOAc=20:1 to afford the product (3.4 g, 49.8%) as colorless oil. LC-MS: (M+H)$^+$=291;

Step 4: Synthesis of 2-(4-(bis(2-chloroethyl)amino)phenyl)acetic acid (B-5). To a round bottom flask was added methyl 2-(4-(bis(2-chloroethyl)amino)phenyl)acetate (B-4) (3.4 g, 11.68 mmol), LiOH (1.7 g, 70.83 mmol), H$_2$O (100 mL) and THF (50 mL). The reaction mixture was stirred at 50° C. for 2 h. After cooled down to r.t., the reaction mixture was adjusted with HCl (1 N) to pH7 and extracted with EtOAc (100 ml*2), the mixture was dried over Na$_2$SO$_4$ and concentrated under reduced pressure. The crude product (2.8 g) was used next step without further purification. LC-MS: (M+H)$^+$=277;

Step 5: Synthesis of 2-(4-(bis(2-chloroethyl)amino)phenyl)-N-(5-((5-tert-butyloxazol-2-yl)methylthio)thiazol-2-yl) acetamide (CY-201). To a stirred methylene chloride solution (20 ml) was added DMAP (438 mg, 3.59 mmol) and 2-(4-(bis(2-chloroethyl)amino)phenyl)acetic acid (B-5) (906 mg, 3.27 mmol). Subsequently, DCC (690 mg, 3.35 mmol) was added to reaction mixture, followed by addition of 5-((5-tert-butyloxazol-2-yl)methylthio)thiazol-2-amine (Intermediate CY-200) (800 mg, 2.97 mmol). The mixture was stirred at r.t for 24 h. After removing dicyclohexylurea (DCU) by filtration, the filtrate was concentrated in vacuum and dried over Na$_2$SO$_4$. The residue was purified by silica gel chromatography eluting with CH$_2$Cl$_2$: EtOAc=20:1 to afford total product (1.2 g, 76%) as a gray solid. LC-MS: (M+H)$^+$=528. $^1$H NMR (300 MHz, CDCl$_3$) δ 10.17 (s, 1H), 7.28-7.30 (m, 1H), 7.17 (d, J=8.4 Hz, 2H), 6.69 (d, J=8.7 Hz, 2H), 6.58 (s, 1H), 3.95 (s, 2H), 363-3.79 (m, 10H), 1.26 (s, 9H).

Biological Assays:
(a) Inhibition of CDK Enzymatic Activity
(a-1) MATERIALS:

CDK1/cyclinB (Accession number for CDK1; GenBank NM 001786, for cyclinB; EMBL M25753): C-terminal 6His-tagged human full length cdk1 (MW=35 kDa), and N-terminal GST-tagged human full length cyclin B (MW=75 kDa) were expressed individually with baculovirus system in Sf21 insect cells. Recombinant proteins were purified using Ni2+/NTA-agarose and GST-agarose, respectively. The cdk1 was then activated using CAK and repurified by Q Sepharose and Ni2+/NTA-agarose. They were then mixed in vitro to form protein complex. The purity of these protein complex was estimated to be 80.5% by SDSPAGE and Coomassie blue staining. Specific Activity of recombinant enzyme was measyre to be 1329 U/mg, where one unit of cdk1/cyclinB activity is defined as 1nmol phosphate incorporated into 0.1 mg/ml histone H1 per minute at 30° C. with a final ATP concentration of 100 mM. Enzyme was stored at concentration of 0.1 mg/ml in 50 mM Tris/HCl pH7.5, 150 mM NaCl, 0.1 mM EGTA, 0.03% Brij-35, 270 mM sucrose, 1mM benzamidine, 0.2 mM PMSF, 0.1% 2-mercaptoethanol.

CDK2/cyclinA (Accession number for CDK2; EMBL M68520, for cyclin A; EMBL X51688): C-terminal 6His-tagged human full length cdk2 (MW=35 kDa), and N-terminal GST-tagged human full length cyclin A (MW=75 kDa) were expressed individually with baculovirus system in Sf21 insect cells. Recombinant cdk2 protein was purified with M2+/NTA agarose and then activated using CAK and repurifed by Q Sepharose and M2+/NTA agarose. Recombinant cyclin A was purified using glutathione-agarose. They were then mixed in vitro to form protein complex. Recombinant protein complex was measured to be 67% in purity with SDS-PAGE and Coomassie blue staining. Specific Activity of purified enzyme was measure to be as 158 U/mg, where one unit of cdk2/cyclinA activity is defined as 1 nmol phosphate incorporated into 0.1 mg/ml histone H1 per minute at 30° C. with a final ATP concentration of 100 mM. Enzyme was stored at a concentration of 0.1 mg/ml in 50 mM Tris/HCl pH7.5, 150 mM NaCl, 0.1 mM EGTA, 0.03% Brij-35, 270 mM sucrose, 1mM benzamidine, 0.2 mM PMSF, 0.1% 2-mercaptoethanol. Frozen solution.

CDK2/cyclinE (Accession number for CDK2; EMBL M68520, for cyclinE1; GenBank NM_001238): C-terminal 6His-tagged, recombinant full-length CDK2 (MW=34 kDa) in complex with N-terminal GST-tagged, recombinant full-length cyclinE1 (MW=74 kDa) were expressed with baculovirus system in Sf21 cells. Recombinant proteins were purified using M2+/NTA agarose and the purity of recombinant protein complex was measured to be around 76% by SDS-PAGE and Coomassie blue staining. Specific Activity of recombinant CDK2/cyclinE was 1336 U/mg, where one unit of CDK2/cylinE1 activity is defined as 1nmol phosphate incorporated into 0.1 mg/ml histone H1 per minute at 30° C. with a final ATP concentration of 100 μM. Enzyme was stored with concentration of 0.1 mg/ml in 50 mM Tris/HCl pH 7.5, 150 mM NaCl, 0.03% Brij-35, 0.1 mM EGTA, 0.2 mM PMSF, 1mM benzamidine, 0.1% 2-mercaptoethanol, 270 mM sucrose.

CDK3/cyclinE (Accession number for CDK3; GenBank X66357, for cyclin E; GenBank NM 001238): C-terminal 6His-tagged recombinant human full-length cdk3 (MW=36 kDa) were coexpressed with N-terminal GST-tagged recombinant human full-length cyclin E (MW=74 kDa) with baculovirus system in Sf21 insect cells. Recombinant protein complex was purified using Ni2+/NTA agarose and with purity to be 66% by SDS PAGE and Coomassie blue staining. Specific Activity of recombinat enzyme was measured to be 861 U/mg, where one unit of cdk3/cyclinE activity is defined as 1nmol phosphate incorporated into 0.1 mg/ml histone H1 per minute at 30° C. with a final ATP concentration of 100 mM. Enzyme was stored at a concentration of 0.1 mg/ml in 50 mM Tris/HCl pH7.5, 150 mM NaCl, 0.1 mM EGTA, 0.03% Brij 35, 270 mM sucrose, 1mM benzamidine, 0.2 mM PMSF, 0.1% 2-mercaptoethanol.

CDK4/cyclinD1 (Accession number for CDK4; NP 000066, for cyclinD1; NP 444284) Recombinant Human Full-length GST-tagged CDK-4 (MW=61.8 kDa) and cyclinD1 (MW=61.2 kDa) were expressed in insect cells. Recombinant enzyme was measure to have specific Activity equal to 190 nmole of phosphate transferred to RbING peptide substrate (INGSPRTPRRGQNR) per minute per mg of total protein at 30° C. Activity was determined at a final protein concentration at 8.33 µg/mL. Enzyme was stored at a concentration of 0.4 mg/ml in 50 mM Tris (pH 7.5), 150 mM NaCl, 0.5 mM EDTA, 0.02% Triton X-100, 2 mM DTT, 50% Glycerol.

CDK6/cyclinD3 (Accession number for CDK6; GenBank X66365, for cyclin D3; EMBL M90814): N-terminal, 6His-tagged full-length human cdk6 (MW=38 kDa) complexed with N-terminal GST-tagged full-length human cyclin D3 (MW=59 kDa) were expressed in Sf21 cells. Recombinant protein complex was purified using glutathione-agarose and activated with CAK, and repurified with M2+/NTA-agarose column Purity was measured to be at least 68%. Specific Activity was measured to be 39 U/mg, where one unit of cdk6/cyclinD3 activity is defined as 1nmol phosphate incorporated into 0.1 mg/ml histone H1 per minute at 30° C. with a final ATP concentration of 100 µM. Enzyme was stored at concentration of 0.1 mg/ml in 50 mM Tris-HCl, pH 7.5, 270 mM sucrose, 150 mM NaCl, ImM benzamidine, 0.2 mM PMSF, 0.1% 2-mercaptoethanol, 0.ImM EGTA, 0.03% Brij 35.

CDK7/cyclinH1/MNAT1 (Accession number for CDK7; NP 001790, for cyclinH1; NP 001230, for MNAT1; NP 002422.1) Recombinant Human Full-Length protein, Histidine-tagged CDK7 (MW=43.2 kDa), Histidine-tagged cyclin H1 (MW=42.6 kDa), Histidine-tagged MNAT1 (MW=40.5 kDa), were expressed in insect cells. Specific Activity of recombinat enzyme complex was measured to be equal to 94 nmole of phosphate transferred to CDK7/9tide substrate (YSPTSPSYSPTSPSYSPTSPSKKKK) per minute per mg of total protein at 30° C. Activity was determined with a final protein concentration at 3.33 µg/mL. Enzyme was stored at a concentration of 0.42 mg/ml in 50 rnM Tris (pH 7.5), 150 mM NaCl, 0.5 mM EDTA, 0.02% Triton X-100, 2 mM DTT, 50% Glycerol.

CDK9/cyclinT1 (Accession number for CDK9; GenBank AF517840, for cyclin T1; GenBank NM 001240) C-terminal 6His-tagged, full-length recombinant, human cdk9 (MW=44 kDa) were co-expressed with untagged, full-length human cyclin T1(MW=80.79 kDa) with baculovirus system in Sf21 insect cells. Recombinat protein complex was purified with $Ni^{2+}$/NTA agarose. Purity of recombinant protein was measured to be 50% by SDS-PAGE and Coomassie blue staining. Specific Activity of purified enzyme was measured to be186 U/mg, where one unit of cdk9/cyclin T1 activity is defined as 1nmol phosphate incorporated into 100 µM PDKtide (KT-FCGTPEYLAPEVRREPRILSEEEQEMFRDFDYIADWC) per minute at 30° C. with a final ATP concentration of 100 µM. Enzyme was stored at concentration of 0.1 mg/ml in 50 mM Tris-HCl, pH 7.5, 300 mM NaCl, 0. ImM EGTA, 0.03% Brij-35, 270 mM sucrose, ImM benzamidine, 0.1% 2-mercaptoethanol, 0.2 mM PMSF. Histon H1 (Substrate for CDK1, 2, 3, 6 and 7): Histone H1 (Sigma cat#H4524), was purified as a lysine rich fraction from calf thymus with 93% purity (MW=21.5 kDa). Purified protein was stored at a concentration of 20 mg/ml=930 µM in distilled water. RBC-CTF (Substrate for CDK4): Human RB protein (S773-K928, MW=44.46 kDa), N-terminal GST-tagged was purified and followed with a factor Xa cleavage, which was performed in 4 mM concentration of glutathione, Purified protein was stocked at a concentration of 0.67 mg/ml. PDKtide (Substrate for CDK9): Synthetic peptide substrate with sequence of [KTFCGTPEYLAPEVRREPRILSEEEQEMFRDFD YIADWC], MW=4771.4

(a-2) Assay Conditions:

For CDK activity assay, p33 ATP tracers were incubated with purified recombinant specific combination of purified CDK kinases, cyclins and substrates to monitor the enzyme activity. In these assays, individual reactions were carried out in specific conditions describe below with reaction buffer: 20 mM HEPES (pH 7.5), 10 mM $MgCl_2$, 1 mM EGTA, 0.02% Brij 35, 0.02 mg/ml BSA, 0.1 mM $Na_3VO_4$, 2 mM DTT. An equal volume of 25% TCA was added to stop the reaction and precipitate the labeled peptides. Precipitated proteins were trapped onto glass fiber B filterplates and excess unlabeled p33 ATP was washed off. The plates were allowed to air-dry prior to the addition of 30 uL/well of Packard Microscint 20. The amount of incorporated isotope was measured using a Perkin Elmer TopCount plate reader. Different concentrations of compounds were added to reaction to assess the activity of compounds to inhibit PDGF-beta kinase. IC50 was calculated using Prism software with sigmoidal dose-response curve fitting.

CDK1/cyclinB: 1 nM CDK1/cyclinB and 20 µM Histon H1 were mixed in the reaction buffer with final concentration of 1 µM ATP and 1% DMSO. Reaction was performed for 2 hours at room temperature and with conversion rate of ATP is equal to 7.5%.

CDK2/cyclinE; 0.5 nM CDK2/cyclinE and 5 µM Histon H1 were mixed in the reaction buffer with final concentration of 1 µM ATP and 1% DMSO. Reaction was incubated for 2 hours at room temperature and conversion rate of ATP is about 4.5%.

CDK3/cyclinE: 0.5 nM CDK3/cyclinE and 20 µM Histon H1 were mixed in the reaction buffer with final concentration of 1 µM ATP and 1% DMSO. Reaction was incubated for 2 hours at room temperature and with conversion rate of ATP was measured to be 7.0%.

CDK4/cyclinD1: 2 nM CDK4/cyclinD1 and 1 µM RB-CTF were mixed in the reaction buffer with final concentration of 1 µM ATP and 1% DMSO. Reaction was incubated for 2 hours at room temperature and with conversion rate of ATP was measured to be 8.5%.

CDK6/cyclinD3: 50 nM CDK6/cyclinD3 and 5 µM Histon H1 were mixed in the reaction buffer with final concentration of 1 µM ATP and 1% DMSO. Reaction was incubated for 2 hours at room temperature and with conversion rate of ATP that was measured to be 13%.

CDK7/cyclinH1/MNAT1: 100 nM CDK7/cyclinH1/MNAT1 and 20 µM Histon H1 were mixed in the reaction buffer with 1 µM ATP and 1% DMSO. Reaction was incubated for 2 hours at room temperature and conversion rate of ATP was measured to be 5.5%.

CDK9/cyclinT1: 2 nM CDK9/cyclinT1 and 20 µM pdk-TIDE were mixed in the reaction buffer with 1 µM ATP and 1% DMSO at final concentrations. Reaction was incubate for 2 hours at room temperature and conversion rate of ATP was measured to be 12%.

Staurosporine was used as reference compound. Such assays, carried out with a range of doses of test compounds, allow the determination of an approximate IC50 value. Although the inhibitory properties of the compounds of the present invention vary with structural change as expected, the activity generally exhibited by these agents is in the range of IC50=0.1-1000 nM.

The following are the structures of the nitrogen mustard drug Chlorambucil and its corresponding CDK-inhibiting derivative CY-201. Both Chlorambucil and CY-201 has a nitrogen mustard pharmacophore capable of alkylating DNA. The following table lists the CDK IC50 values of CY-201 which clearly shows that CY-201 is a very potent CDK inhibitor. Therefore, CY-201, as far as we know, represents the First-in-Class dual-functional nitrogen mustard/CDK inhibitor.

Chlorambucil
The Parental DNA-alkylating Nitrogen Mustard

CY-201
CDK Inhibiting Derivatives of Chlorambucil

| CDK subtype | CY-301 (nM) | Staurosporine (nM) | Chlorambucil |
|---|---|---|---|
| CDK2/cyclin E | 2.7 | 1.0 | No activity |
| CDK3/cyclin E | 45.62 | 4.12 | No activity |
| CDK9/cyclin T1 | 90.44 | 6.56 | No activity |

(b) In Vitro Anti-Proliferation Assay:

The human tumor cell lines are grown in RPMI 1640 medium containing 5% fetal bovine serum and 2 mM L-glutamine. For a typical experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 h prior to addition of experimental drugs. After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration and stored frozen prior to use. At the time of drug addition, an aliquot of frozen concentrate is thawed and diluted to twice the desired final maximum test concentration with complete medium containing 50 μg/ml gentamicin. Additional four, 10-Fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (T1)], the percentage growth is calculated at each of the drug concentrations levels. Percentage growth inhibition is calculated as:

$[(Ti-Tz)/(C-Tz)] \times 100$ for concentrations for which $Ti >/= Tz$ $[(Ti-Tz)/Tz] \times 100$ for concentrations for which $Ti < Tz$.

Three dose response parameters are calculated for each experimental agent. Growth inhibition of 50% (GI50) is calculated from $[(Ti-Tz)/(C-Tz)] \times 100 = 50$, which is the drug concentration resulting in a 50% reduction in the net protein increase (as measured by SRB staining) in control cells during the drug incubation. Such assays, carried out with a range of doses of test compounds, allow the determination of an approximate IC50 value for the in vitro cell antiproliferation assay of cancer cell lines. Although the inhibitory properties of the compounds of the present invention vary with structural change as expected, the activity generally exhibited by these agents is in the range of IC50=0.001-100 uM.

The following table lists the IC50 values of the nitrogen mustard Chlorambucil and its CDK-inhibiting derivative CY-201 in the cellular anti-proliferative assays. The present inventors have surprisingly found that the anti-tumor activities of the CDK inhibiting derivative CY-201 are dramatically improved as compared to the parental drug Chlorambucil. For example, in the melanoma cell line MDA-MS-435, CY-201 is more than 1,500 fold more potent than the parental drug Chlorambucil.

| Cancer | Cell Line | Chlorambucil (uM) | CY-201 (uM) | Ratio |
|---|---|---|---|---|
| Multiple Myeloma | RPMI-8226 | 75.5 | 0.269 | 280.5 |
| Breast Cancer | MDA-MB-231 | 159.2 | 0.219 | 727.8 |

-continued

| Cancer | Cell Line | Chlorambucil (uM) | CY-201 (uM) | Ratio |
|---|---|---|---|---|
| Colon Cancer | SW-620 | 87.5 | 0.098 | 895.4 |
| Melanoma | M14 | 62.4 | 0.058 | 1083.9 |
| Ovarian Cancer | IGROV1 | 116.7 | 0.107 | 1088.9 |
| Colon Cancer | HT29 | 131.5 | 0.107 | 1227.4 |
| Breast Cancer | HS 578T | 188.4 | 0.148 | 1273.5 |
| NSCLC | NCI-H322M | 204.2 | 0.148 | 1380.4 |
| Colon Cancer | KM12 | 143.2 | 0.091 | 1570.4 |
| Melanoma | MDA-MB-435 | 125.3 | 0.079 | 1577.6 |

As we know, CDK2 are the last gatekeeper of DNA damage signaling pathway (DNA damage=>ATM/ATR=>Chk=>p53=>p21=>CDK2/Cyclin E=>G1/S arrest). The inhibition of CDK2 will strongly arrest G1/S transition and stop the cancer cells from uncontrolled proliferation; In addition, recent evidence indicates that CDK2 is involved in cell cycle independent functions such as DNA damage repair. It emerges that CDK2 is necessary for proper DNA repair. Therefore, the inhibition of CDK2 will inhibit DNA damage repair. Furthermore, the evasion from apoptosis (e.g DNA damage-induced apoptosis) is hallmark of cancer. CDK inhibition eventually lead to strong apoptosis after cell cycle arrest since the DNA repair pathway is damaged by CDK inhibition. Taken together, with a quadruple capability of damaging DNA, stopping cell cycle progression, inhibiting DNA damage repair, and inducing strong apoptosis, the dual-targeting CY-201 has dramatically enhanced anti-cancer activities as compared to the single-functional parental DNA alkylating nitrogen mustard drug Chlorambucil.

What is claimed is:

1. A compound of Formula (1):

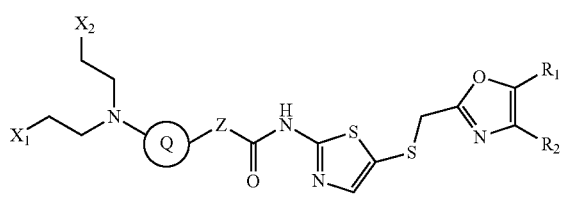

Formula (1)

wherein
each of $X_1$ and $X_2$ independently, is halo or $OSO_2R_a$, in which $R_a$ is alkyl, alkenyl, or alkynyl;
Q is cycloalkyl, cycloalkenyl, heterocycloalkenyl, aryl, or heteroaryl, each of which, independently, is optionally substituted with alkyl, alkenyl, alkynyl, cycloalkyl, heterocycloalkyl, cycloalkenyl, heterocycloalkenyl, aryl, heteroaryl, halo, nitro, oxo, —CH=NH, cyano, alkyl-$R_b$, CH=$NOR_b$, $OR_b$, $OC(O)R_b$, $OC(O)OR_b$, $OC(O)SR_b$, $SR_b$, $C(O)R_b$, $C(O)OR_b$, $C(O)SR_b$, $C(O)NR_cR_d$, $SOR_b$, $SO_2R_b$, $NR_cR_d$, alkyl-$NR_cR_d$, or $N(R_c)C(O)R_d$, in which each of $R_b$, $R_c$, and $R_d$, independently, is H, alkyl, alkenyl, alkynyl, cycloalkyl, heterocycloalkyl, aryl, heteroaryl, halo, cyano, nitro, amino, hydroxyl, alkylamino, haloalkyl, or alkoxy;
Z is deleted or $(CH_2)_m$ in which m is an integer from 1 to 10; and
each of $R_1$ and $R_2$ independently, is H, alkyl, alkenyl, alkynyl, cycloalkyl, heterocycloalkyl, cycloalkenyl, heterocycloalkenyl, aryl, heteroaryl, halo, nitro, —CH=NH, cyano, alkyl-$R_b$, CH=$NOR_b$, $OR_b$, $OC(O)R_b$, $OC(O)OR_b$, $OC(O)SR_b$, $SR_b$, $C(O)R_b$, $C(O)OR_b$, $C(O)SR_b$, $C(O)NR_cR_d$, $SOR_b$, $SO_2R_b$, $NR_cR_d$, alkyl-$NR_cR_d$, or $N(R_c)C(O)R_d$.

2. The compound of claim 1, wherein $R_1$ is H, alkyl, alkenyl, or alkynyl and $R_2$ is H.

3. A compound of claim 2 represented by Formula (2)

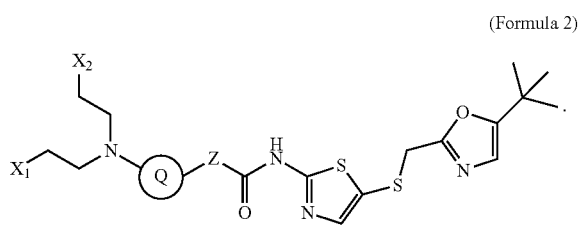

(Formula 2)

4. The compound of claim 3, wherein Q is an aryl or heteroaryl.

5. The compound of claim 4, wherein Q is a 5-6 membered aryl or heteroaryl.

6. The compound of claim 1, represented by Formula (3)

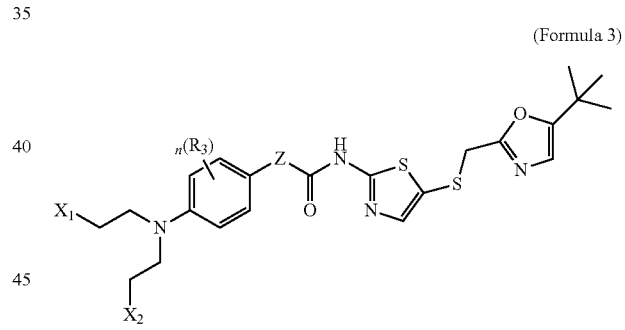

(Formula 3)

wherein $R_3$ is H or nitro; n is 0, 1, 2, or 3.

7. The compound of claim 4, wherein Q is a 9-10 membered aryl or heteroaryl.

8. The compound of claim 1 represented by Formula (4)

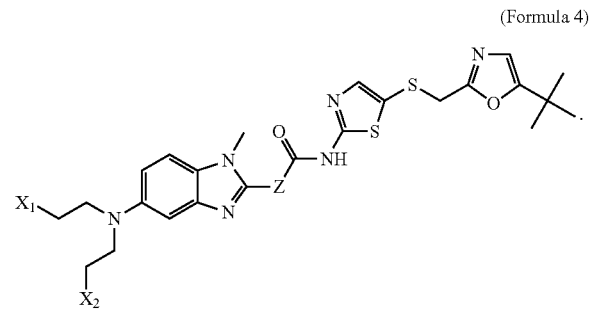

(Formula 4)

9. A compound of claim 1, wherein the compound is
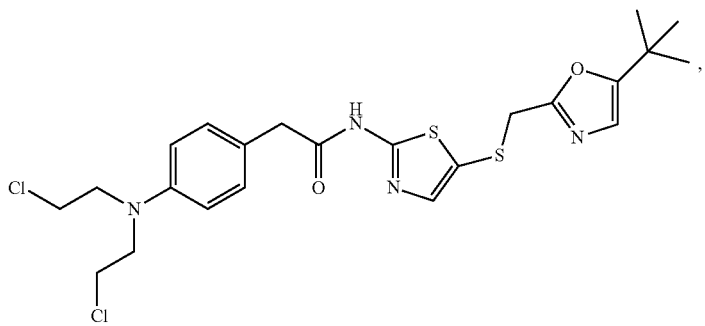
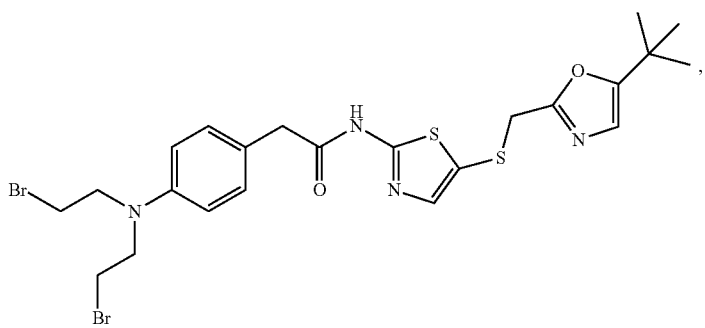
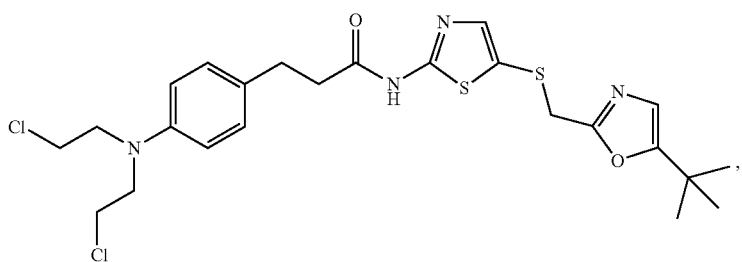
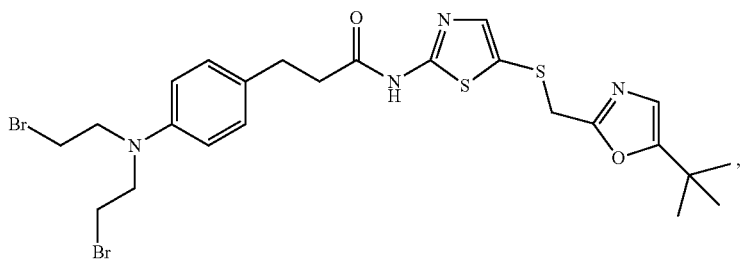
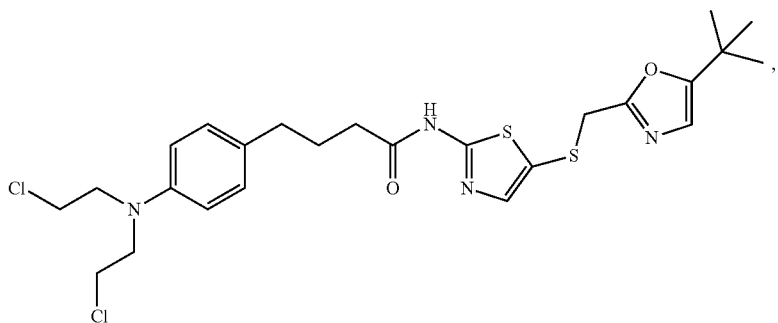

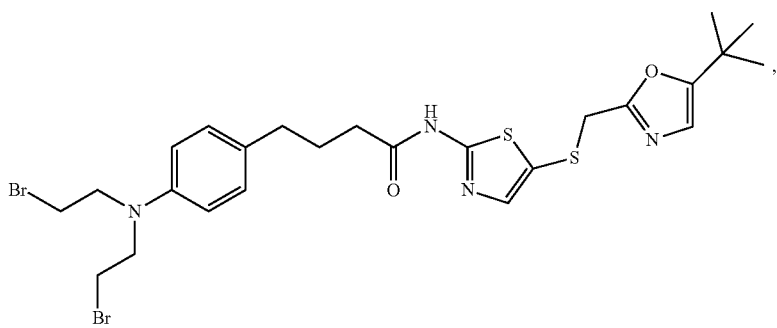
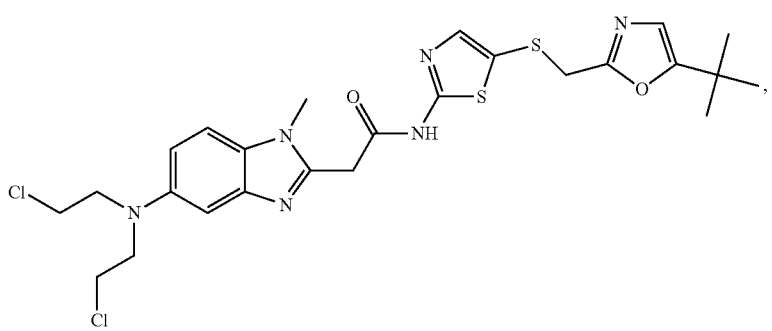
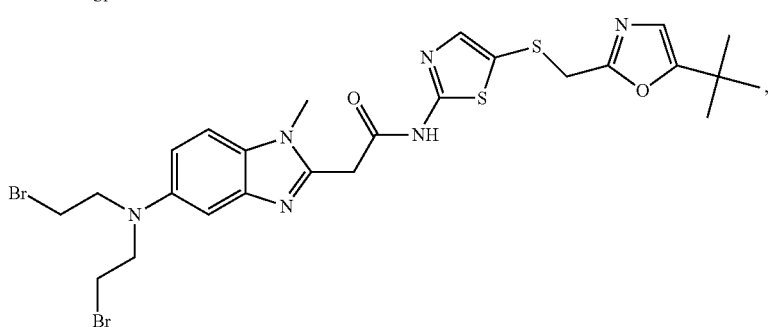
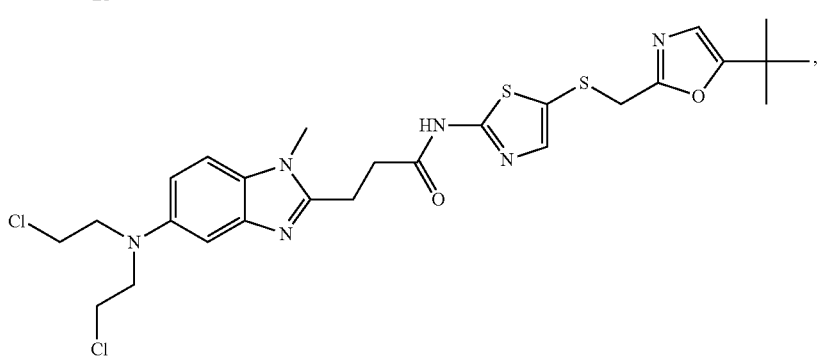
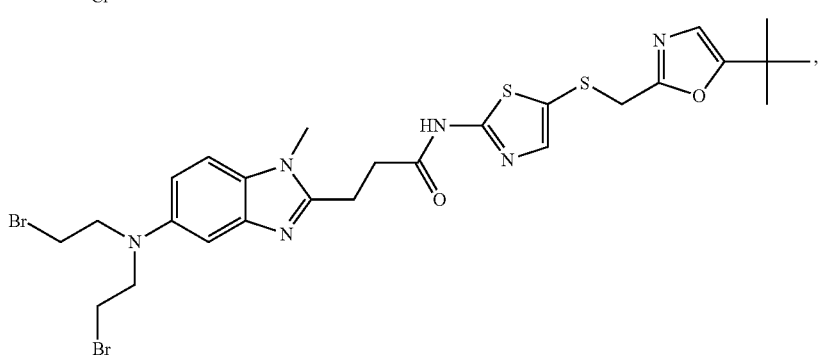

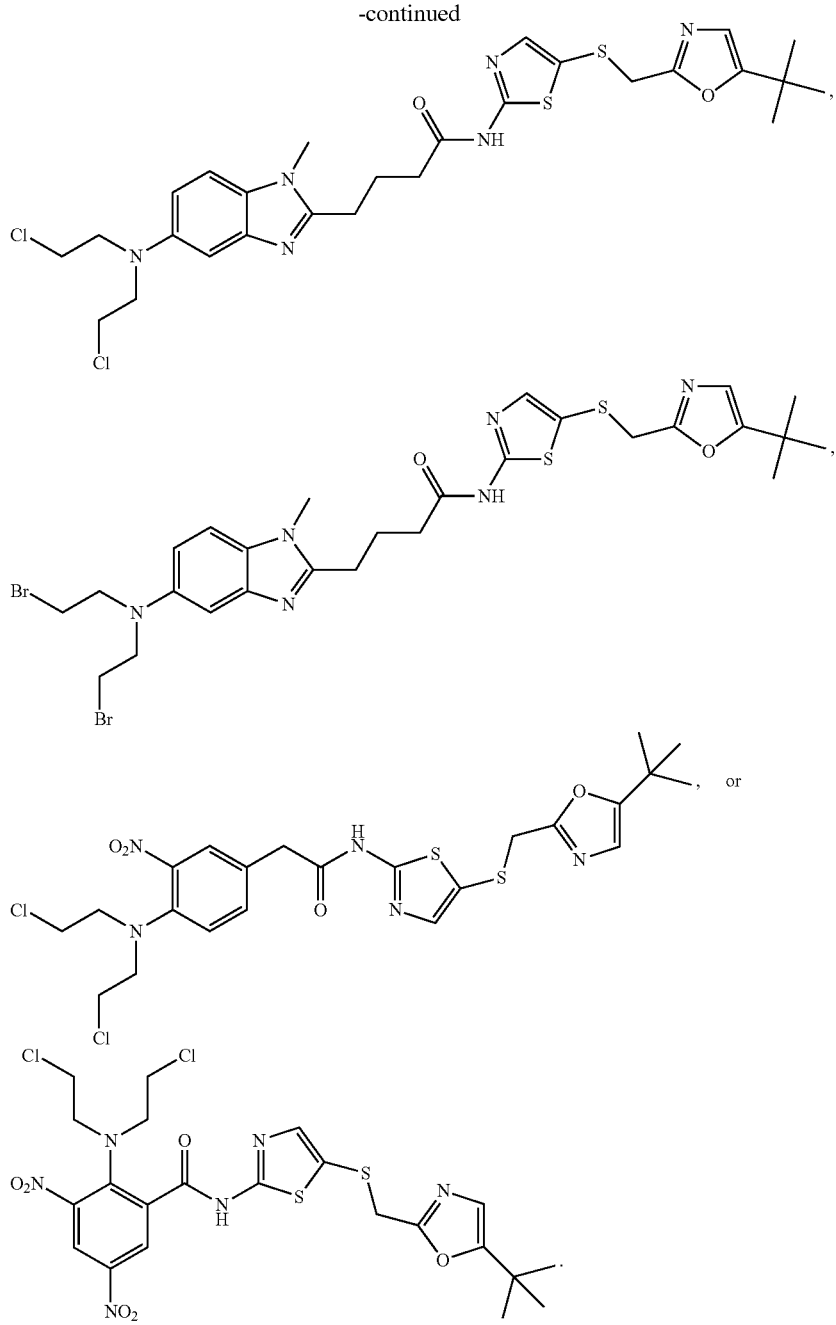
10. A compound of claim 1, wherein the compound is
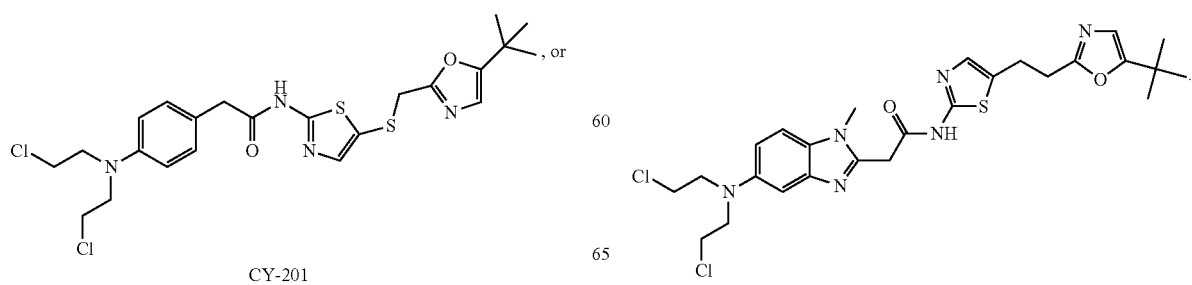

11. A compound of claim 1, wherein the compound is

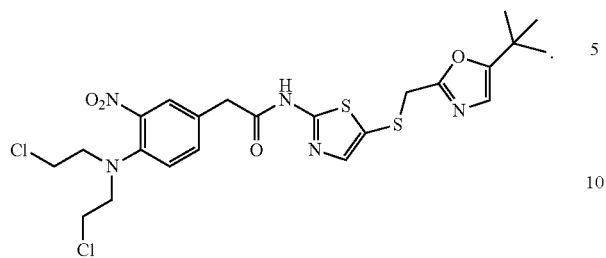

12. A pharmaceutical composition comprising a compound of claim 1 and a pharmaceutically acceptable carrier.

13. A method of improving or relieving a neoplastic cancer, colon cancer, melanoma, ovarian cancer, and non-small cell lung cancer, the method comprising administering to a subject in need thereof an effective amount of a compound of claim 1.

* * * * *